US010081005B2

(12) United States Patent
Moore et al.

(10) Patent No.: US 10,081,005 B2
(45) Date of Patent: Sep. 25, 2018

(54) AUTOMATED, MULTI-POT HIGH-PRESSURE RADIO-SYNTHESIZER FOR PRODUCTION OF PET TRACERS

(71) Applicant: THE REGENTS OF THE UNIVERSITY OF CALIFORNIA, Oakland, CA (US)

(72) Inventors: Melissa Moore, Los Angeles, CA (US); R. Michael Van Dam, Los Angeles, CA (US); Kevin Quinn, Irvine, CA (US); Shane Claggett, Los Angeles, CA (US); Henry Herman, Los Angeles, CA (US); Mark Lazari, North Hills, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 540 days.

(21) Appl. No.: 14/777,973

(22) PCT Filed: Mar. 26, 2014

(86) PCT No.: PCT/US2014/031905
§ 371 (c)(1),
(2) Date: Sep. 17, 2015

(87) PCT Pub. No.: WO2014/160799
PCT Pub. Date: Oct. 2, 2014

(65) Prior Publication Data
US 2016/0280734 A1    Sep. 29, 2016

Related U.S. Application Data

(60) Provisional application No. 61/805,879, filed on Mar. 27, 2013, provisional application No. 61/805,411, filed on Mar. 26, 2013.

(51) Int. Cl.
B01J 19/00    (2006.01)
B01J 14/00    (2006.01)
C07H 17/02    (2006.01)

(52) U.S. Cl.
CPC .............. B01J 19/004 (2013.01); B01J 14/00 (2013.01); B01J 19/0093 (2013.01);
(Continued)

(58) Field of Classification Search
CPC ...... B01J 19/0093; B01J 19/004; B01J 14/00; B01J 2219/00986; B01J 2219/00831;
(Continued)

(56) References Cited

U.S. PATENT DOCUMENTS

2006/0245980 A1    11/2006    Kiselev et al.
2012/0108858 A1    5/2012    Kiselev
2013/0020727 A1    1/2013    Klausing et al.

FOREIGN PATENT DOCUMENTS

JP    2009-047454 A    3/2009
KR    10-2013-002795 A    3/2013

OTHER PUBLICATIONS

PCT International Preliminary Report on Patentability (Chapter I of the Patent Cooperation Treaty) for PCT/US2014/031905, Applicant: The Regents of the University of California, Form PCT/IB/326 and 373, dated Oct. 8, 2015 (7pages).
(Continued)

Primary Examiner — Lessanework T Seifu
(74) Attorney, Agent, or Firm — Vista IP Law Group LLP

(57) ABSTRACT

An automated radiosynthesizer device includes a plurality of reactor assemblies, each reactor assembly being operatively connected to a horizontal actuator for moving the reactor assembly in the horizontal direction and a vertical actuator for moving the reactor assembly in the vertical direction. A plurality of disposable cassettes are disposed above each of
(Continued)

the plurality of reactor assemblies, each cassette comprising a lower surface comprising a plurality of sealed and un-sealed gaskets, wherein the un-sealed gaskets are connected to internal fluid paths within the cassette. The device includes a three-axis reagent and gas handling robot disposed above the plurality of cassettes and terminates in a vial gripper and a gas manifold having an inert gas port and a vacuum port. The device includes a control system configured to control the horizontal actuator and vertical actuator of each reactor assembly and the three-axis reagent and gas handling robot.

20 Claims, 16 Drawing Sheets

(52) U.S. Cl.
CPC ....... *C07H 17/02* (2013.01); *B01J 2219/0097* (2013.01); *B01J 2219/00799* (2013.01); *B01J 2219/00801* (2013.01); *B01J 2219/00813* (2013.01); *B01J 2219/00815* (2013.01); *B01J 2219/00817* (2013.01); *B01J 2219/00831* (2013.01); *B01J 2219/00873* (2013.01); *B01J 2219/00889* (2013.01); *B01J 2219/00909* (2013.01); *B01J 2219/00918* (2013.01); *B01J 2219/00986* (2013.01)

(58) Field of Classification Search
CPC .... B01J 2219/00909; B01J 2219/00815; B01J 2219/00889; B01J 2219/00813; B01J 2219/0097; B01J 2219/00817; B01J 2219/00799; B01J 2219/00873; B01J 2219/00918; B01J 2219/00801; B01J 2219/00686; B01J 2219/00689; B01J 2219/00691
See application file for complete search history.

(56) References Cited

OTHER PUBLICATIONS

Alauddin, Mian M. et al., Synthesis of [18F]-labeled adenosine analogues as potential PET imaging agents, J Label Compd Radiopharm 2003; 46: 805-814.
Alauddin, Mian M. et al., Synthesis of [18F]-labeled 2'-deoxy-2'-fluoro-5-methyl-1-B-D-arabinofuranosyluracil([18F]-FMAU), J Label Compd Radiopharm 2002; 45: 583-590.
Anderson, Harry et al., Improved synthesis of 2'-deoxy-2'-[18F]-fluoro-1-B-D-arabinofuranosyl-5-iodouraci ([18F]-FIAU), Nuclear Medicine and Biology 37 (2010) 439-442.
Cai, Hangcheng et al., The improved synthesis of 5-substituted 2'-[18F]fluoro-2'-deoxy-arabinofuranosyluracil derivatives ([18F]FEAU, [18F]FFAU, [18F]FCAU, [18F]FBAU and [18F]FIAU) using a multistep one-pot strategy, Nuclear Medicine and Biology 38 (2011) 659-666.
Chin, Frederick T. et al., Semiautomated Radiosynthesis and Biological Evaluation of [18F]FEAU: A Novel PET Imaging Agent for HSV1-tk/sr39tk Reported Gene Expression, Mol Imaging Biol (2008) 10:82-91.
Coenen, H.H. et al., Fluorine-18 radiopharmaceuticals beyong [18F]FDG for use in oncology and neurosciences, Nuclear Medicine and Biology 37 (2010) 727-740.
Herman, Henry et al., Multi-pot radiosynthesizer capable of high-pressure reactions for production of [18F]FAC and analogs, J. Nucl Med. 2011; 52 (Supplement 1):1440.
Herman, Henry et al., Flexible radiosynthesizer capable of multi-pot high temperature and pressure reactions, Crump Institute Molecular Imaging, UCLA, Department of Molecular & Medical Pharmacology, UCLA, Sofie Biosciences, Inc. (PPT) (2011) (24pages).
Herman, Henry et al., Flexible radiosynthesizer capable of multi-pot high temperature and pressure reactions, Crump Institute Molecular Imaging, UCLA, Department of Molecular & Medical Pharmacology, UCLA, Sofie Biosciences, Inc. (Abstract) (2011) (1page).
Keng, Pei Yuin et al., Emerging Technologies for Decentralized Production of PET Tracers, Positron Emission Tomography—Current Clinical and Research Aspects, www.intechopen.com, InTech; 2012; 153-182.
Li, Zibo et al., Automated synthesis of 2'-deoxy-2'-[18F]fluoro-5-methyl-1-B-D-arabinofuranosyluracil ([18F]-FMAU) using a one reactor radiosynthesis module, Nuclear Medicine and Biology 38 (2011) 201-206.
Moore, Melissa D. et al., ARC-P HS+: A versatile radiosynthesizer for the production of PET tracers, AACR Annual Meeting, Mar. 31-Apr. 4, 2012, Chicago, IL (1page).
Paolillo, Vincenzo et al., A fully automated synthesis of [18F]-FEAU and [18F]-FMAU using a novel dual reactor radiosynthesis module, J. Label Compd. Radiopharm 2009, 52, 553-558.
Sachinidis, John I et al., Automation for Optimised Production of Fluorine-18-Labelled Radiopharmaceuticals, Current Radiopharmaceuticals, 2010, 3, 248-253.
PCT International Search Report for PCT/US2014/031905, Applicant: The Regents of the University of California, Form PCT/ISA/210 and 220, dated Jul. 25, 2014 (5pages).
PCT Written Opinion of the International Search Authority for PCT/US2014/031905, Applicant: The Regents of the University of California,, Form PCT/ISA/237, dated Jul. 25, 2014 (5pages).
Herman, Henry et al., Flexible radiosynthesizer capable of multi-pot high temperature and pressure reactions, Crump Institute Molecular Imaging, UCLA, Department of Molecular & Medical Pharmacology, UCLA, Sofie Biosciences, Inc. (Abstract) (2011), (1page).

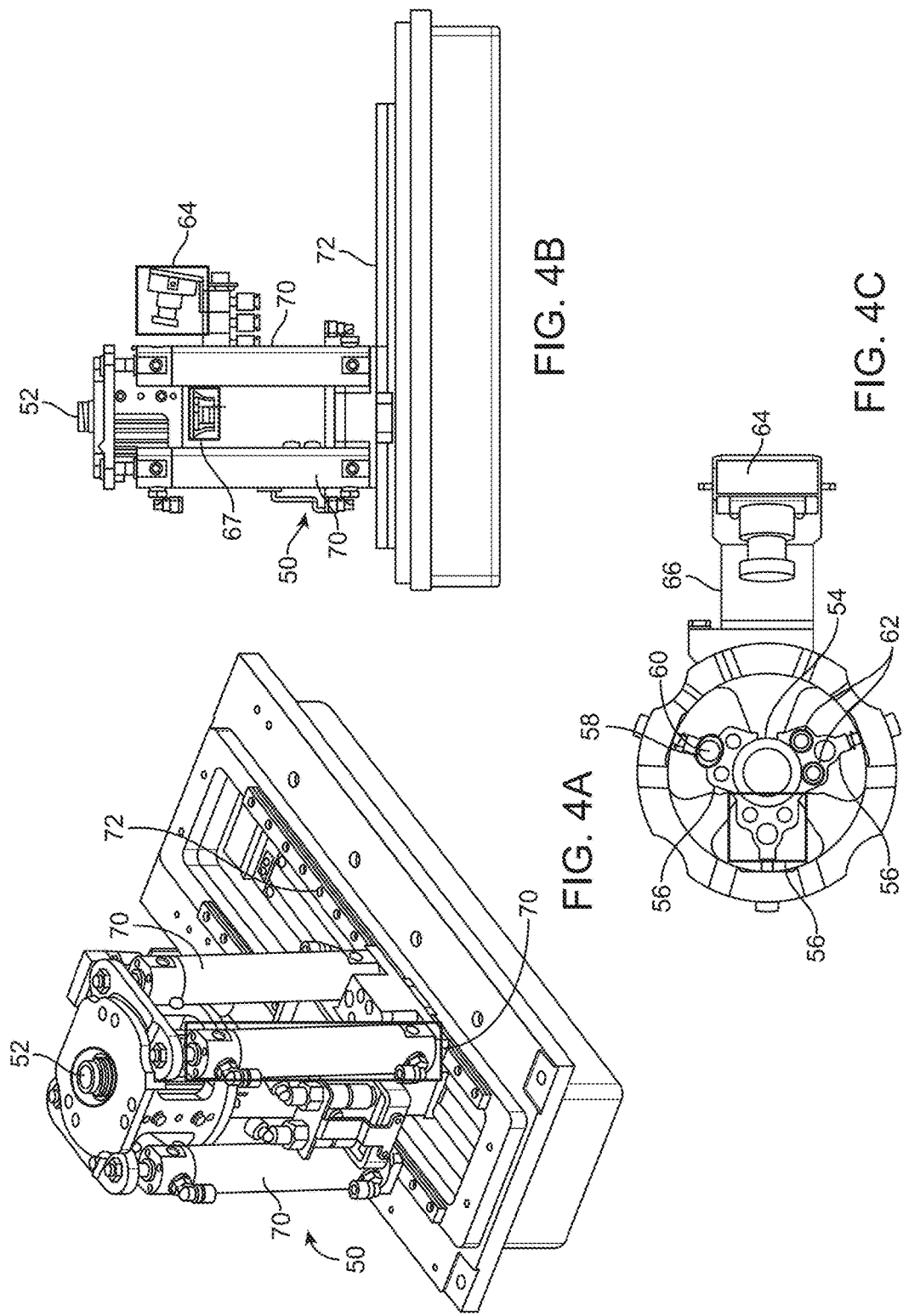

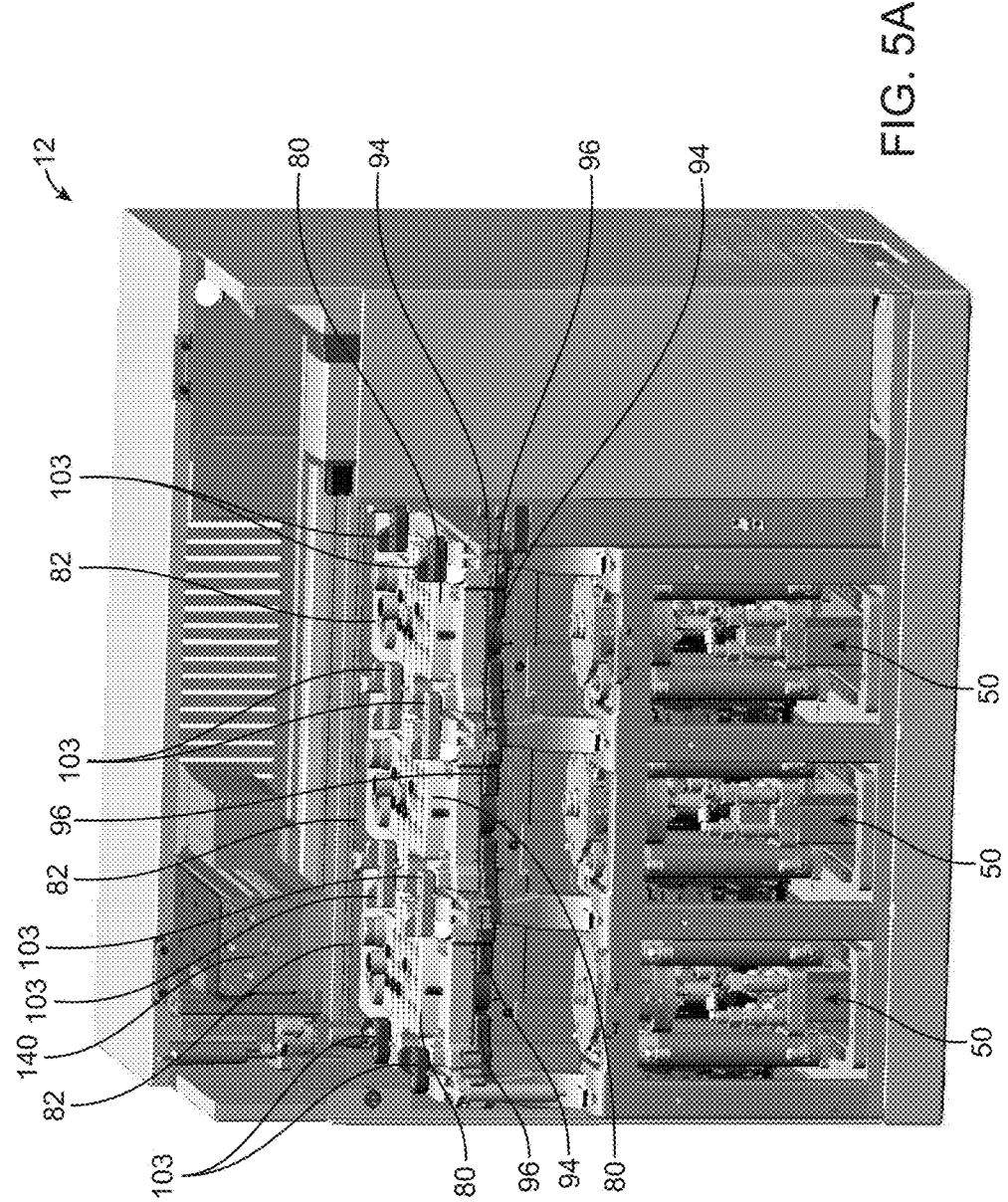

REACT
POSITION #2

ADDITION

TRANSFER

ADDITION

AUTOMATED, MULTI-POT HIGH-PRESSURE RADIO-SYNTHESIZER FOR PRODUCTION OF PET TRACERS

CROSS-REFERENCE TO RELATED APPLICATIONS

This Application is a U.S. National Stage filing under 35 U.S.C. § 371 of PCT Patent Application No. PCT/US2014/031905, filed Mar. 26, 2014, which claims priority to U.S. Provisional Patent Application No. 61/805,411 filed on Mar. 26, 2013 and U.S. Provisional Patent Application No. 61/805,879 filed on Mar. 27, 2013. The contents of the aforementioned applications are incorporated by reference herein. Priority is expressly claimed in accordance with 35 U.S.C. 119, 120, 365 and 371 and any other applicable statutes.

STATEMENT REGARDING FEDERALLY SPONSORED RESEARCH AND DEVELOPMENT

This invention was made with Government support under DE-FG02-06ER64249 and DE-SC0001249, awarded by the Department of Energy. The Government has certain rights in the invention.

TECHNICAL FIELD

The technical field generally relates to devices and system used in radiochemistry applications and, more specifically, devices and systems for the automated synthesis of positron emission tomography (PET) tracers.

BACKGROUND

Positron emission tomography (PET) has opened the door to in vivo imaging for the purposes of non-invasive disease detection, cancer staging, and drug efficacy screening. The most commonly used PET tracer is 2-[$^{18}$F]fluoro-2-deoxy-D-glucose ([$^{18}$F]FDG) due to its relative ease of production, manageable half-life, and ubiquitous application. The increased demand for [$^{18}$F]FDG has led to the development of a variety of automated radiosynthesizers to lower its cost, enable its production at many different sites, and reduce the radiation exposure of the radiochemist. Automated radiosynthesizers are vital for routine production of PET tracers to minimize radiation exposure to operators and to ensure reproducible synthesis yields.

Though automated synthesis of [$^{18}$F]FDG is extremely valuable, there are many $^{18}$F-labeled PET tracers that await an automated synthesizer to streamline their production. Some of these tracers require high pressures, complicated chemistries, and/or corrosive reagents that make automation very complicated and difficult. For example, nucleoside analogs that have been used in imaging cell proliferation, reporter gene expression, and as possible screening agents for chemotherapy drug efficacy often require high temperature reactions in volatile solvents. Several attempts have been made to automate the syntheses of these tracers on commercially available radiosynthesizers, but have required modifications to the chemistry (e.g. use of alternative solvents or reduced temperatures) to reduce the pressures involved and avoid exceeding the limitations of the radiosynthesizers.

The recent trend in the synthesizer industry towards the use of disposable kits aims to simplify setup and operation for the user, but often introduces several limitations related to temperature and chemical compatibility, thus requiring re-optimization of protocols developed on non-cassette-based systems. Radiochemists would benefit from a single hybrid system that provides tremendous flexibility for development and optimization of reaction conditions while also providing a pathway to simple, cassette-based production of diverse tracers.

SUMMARY

In one aspect of the invention, an automated radiosynthesizer device includes a plurality of reactor assemblies, each reactor assembly of the plurality being operatively connected to a horizontal actuator for moving the reactor assembly in the horizontal direction and a vertical actuator for moving the reactor assembly in the vertical direction. The device further includes a plurality of disposable cassettes disposed above each of the plurality of reactor assemblies, each disposable cassette comprising a lower surface comprising a plurality of sealed and un-sealed gaskets, wherein the un-sealed gaskets are connected to internal fluid paths within the disposable cassette. A reagent and gas handling robot is disposed above the plurality of disposable cassettes and comprising an x-axis actuator, a y-axis actuator, a first z-axis actuator, and a second z-axis actuator, wherein the first z-axis actuator is operatively coupled to a vial gripper and the second z-axis actuator is operatively coupled to a gas manifold. The device includes a control system configured to control the horizontal actuator and vertical actuator of each reactor assembly and the reagent and gas handling robot.

In another aspect of the invention, an automated method of performing radiosynthesis using a device having a plurality of reactor assemblies is disclosed. Each reactor assembly of the plurality is moveable in a vertical and horizontal direction. The device includes a plurality of disposable cassettes disposed above each of the plurality of reactor assemblies, each disposable cassette comprising a lower surface comprising a plurality of sealed and un-sealed gaskets, wherein the un-sealed gaskets are connected to internal fluid paths within the disposable cassette. The device includes a reagent and gas handling robot disposed above the plurality of disposable cassettes; and a control system configured to control the movement of the reactor assemblies and the reagent and gas handling robot. The method includes moving a reactor vial contained in a first reactor assembly vertically against one or more of the sealed and unsealed gaskets of a first disposable cassette and performing one or more of the following operations on a radiosynthesis reagent or precursor contained in the reactor vial: addition, evaporation, and reaction. A reactor vial contained in a second reactor assembly is moved vertically against one or more of the sealed and unsealed gaskets of a second disposable cassette and the radiosynthesis reagent or precursor is transferred to a second disposable cassette and into the reactor vial contained in the second reactor. In the reactor vial contained in the second reactor, one or more of the following operations is performed on a radiosynthesis reagent or precursor contained in the reactor vial: addition, evaporation, reaction. A final radiosynthesis product can be transferred to a collection vial or it can be transferred to an HPLC injection valve.

In some embodiments, a reactor vial contained in a third reactor assembly is moved vertically against one or more of the sealed and unsealed gaskets of a third disposable cassette. The radiosynthesis reagent or precursor is then transferred to a third disposable cassette and into the reactor vial contained in the third reactor. In the reactor vial of the third reactor, one or more of the following operations is performed on a radiosynthesis reagent or precursor contained in the reactor vial: addition, evaporation, reaction.

In another embodiment, an automated method of performing radiosynthesis using a device having a plurality of reactor assemblies is provided. Each reactor assembly of the plurality is moveable in a vertical and horizontal direction. The device also includes a plurality of disposable cassettes disposed above each of the plurality of reactor assemblies, each disposable cassette comprising a lower surface comprising a plurality of sealed and un-sealed gaskets, wherein the un-sealed gaskets are connected to internal fluid paths within the disposable cassette. The device also includes a reagent and gas handling robot disposed above the plurality of disposable cassettes and a control system configured to control the movement of the reactor assemblies and the reagent and gas handling robot. The method includes actuating the reagent gas handling robot to place a vacuum port and an inert gas port into corresponding ports on the disposable cassette and moving a reactor vial contained in a first reactor assembly vertically against one or more of the unsealed gaskets of the disposable cassette and performing evaporation on a radiosynthesis reagent or precursor contained in the reactor vial.

In another embodiment, an automated method of performing radiosynthesis using a device having a plurality of reactor assemblies is provided. Each reactor assembly of the plurality is moveable in a vertical and horizontal direction. The device also includes a plurality of disposable cassettes disposed above each of the plurality of reactor assemblies, each disposable cassette comprising a lower surface comprising a plurality of sealed and un-sealed gaskets, wherein the un-sealed gaskets are connected to internal fluid paths within the disposable cassette. The device also includes a reagent and gas handling robot disposed above the plurality of disposable cassettes and a control system configured to control the movement of the reactor assemblies and the reagent and gas handling robot. The method includes actuating the reagent gas handling robot to place a reagent vial into a reagent addition position on the disposable cassette and actuating the reagent gas handling robot to place an inert gas port into a corresponding port on the disposable cassette. A reactor vial contained in a first reactor assembly is vertically moved against one or more of the unsealed gaskets of the disposable cassette and performing an addition operation in the reactor vial whereby contents of the reagent vial are transferred to the reactor vial.

In another embodiment, an automated method of performing radiosynthesis using a device having a plurality of reactor assemblies is provided. Each reactor assembly of the plurality is moveable in a vertical and horizontal direction. The device also includes a plurality of disposable cassettes disposed above each of the plurality of reactor assemblies, each disposable cassette comprising a lower surface comprising a plurality of sealed and un-sealed gaskets, wherein the un-sealed gaskets are connected to internal fluid paths within the disposable cassette. The device also includes a reagent and gas handling robot disposed above the plurality of disposable cassettes and a control system configured to control the movement of the reactor assemblies and the reagent and gas handling robot. The method includes moving a reactor vial contained in a first reactor assembly vertically against one or more of the sealed and unsealed gaskets of a first disposable cassette to manufacture a first PET tracer. A reactor vial contained in a second reactor assembly is vertically moved against one or more of the sealed and unsealed gaskets of a second disposable cassette to manufacture a second PET tracer. The first PET tracer and the second PET tracer are transferred respective collection vials.

In another embodiment, an automated radiosynthesizer device includes a plurality of reactor assemblies, each reactor assembly of the plurality being operatively connected to a horizontal actuator for moving the reactor assembly in the horizontal direction and a vertical actuator for moving the reactor assembly in the vertical direction. A plurality of disposable cassettes are disposed above each of the plurality of reactor assemblies, each disposable cassette comprising a lower surface comprising a plurality of sealed and un-sealed gaskets, wherein the un-sealed gaskets are connected to internal fluid paths within the disposable cassette. The device includes a three-axis reagent and gas handling robot disposed above the plurality of disposable cassettes and comprising a vial gripper and a gas manifold having an inert gas port and a vacuum port. The device includes a control system configured to control the horizontal actuator and vertical actuator of each reactor assembly and the three-axis reagent and gas handling robot.

BRIEF DESCRIPTION OF THE DRAWINGS

FIG. 4A illustrates a perspective view of a single reactor assembly contained within a horizontal actuator.

FIG. 4B illustrates a side view of the single reactor assembly of FIG. 4A.

FIG. 4C illustrates a top down view of single reactor assembly illustrated in FIG. 4B.

FIG. 5A illustrates a synthesizer according to one embodiment.

DETAILED DESCRIPTION OF ILLUSTRATED EMBODIMENTS

Figure 1:
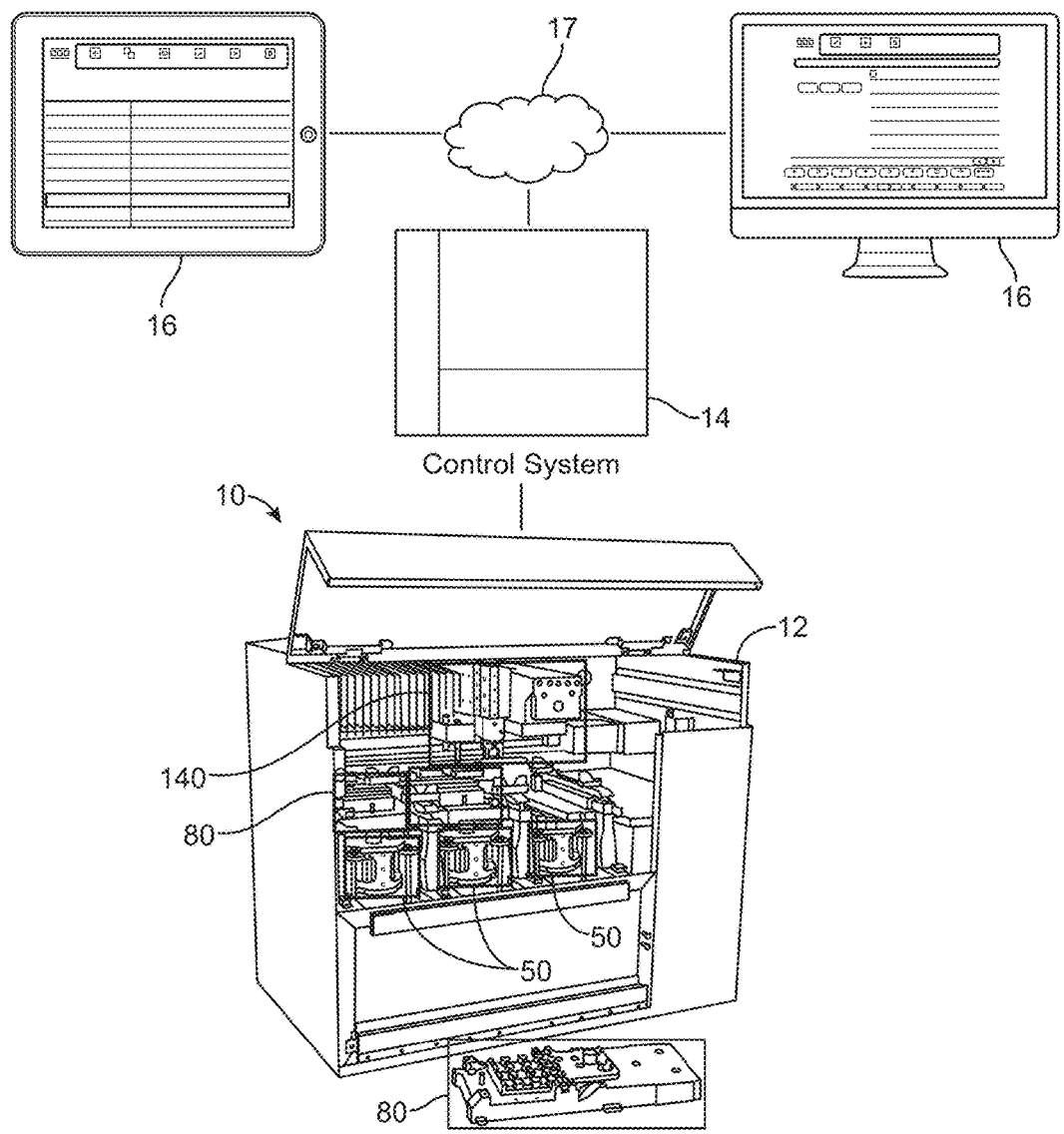
FIG. 1 illustrates an automated radiosynthesizer according to one embodiment.

FIG. 1 illustrates an automated radiosynthesizer 10 according to one embodiment. The automated radiosynthesizer 10 includes a synthesizer 12 where the chemical operations take place to generate a desired radiochemical product such as PET tracer. The synthesizer 12 is controlled by control that interfaces with the synthesizer 12. The control system 14 is used to drive the various hardware components of the synthesizer 12 as described in more detail below. In one aspect of the invention, various client devices 16 can interface with the control system 16 to operate the automated radiosynthesizer 10. For example, the client devices 16 can be used to create or edit various synthesis programs to produce a desired radiochemical product. The client devices 16 may also be used to observe a radiosynthesis run that is currently in progress. The client devices 16 may include a computer such as a laptop or desktop computer or client devices may include mobile devices such as tablets (e.g., Apple iPad, iPhone, and the like), Smartphones (e.g., phones running Google's Android software) and the like. The client devices 16 can interface with the control system 16 using either a dedicated application running on the client device 16 or by using a web browser application. The software that is used as part of the client device 16 may run on a number of different operating systems. Client devices 16 interface with the control system 14 over a network 17 such as a LAN, WAN, or the like. Connections may be wired or wireless.

As explained herein, the client device 16 can be used to create or edit various synthesis programs to produce the desired radiochemical product. Radiochemistry systems are typically programmed at the level of individual valves and other components, requiring a detailed understanding of the underlying system hardware. Such an approach necessitates a significant learning curve to become familiar with the particular system details and the programming language/interface such that creation and optimization of a desired synthesis can be accomplished. The software used with the client device 16 introduces a new paradigm that strives to eliminate these unnecessary complexities and instead allows the end user to describe the synthesis in terms that make intuitive sense to a chemist or radiochemist that may have no prior experience with automated systems.

A new synthesis protocol is created in two stages: (1) the reagents that will be used in the synthesis are described, and (2) the program is built by stringing together an ordered sequence of unit operations. The user can switch back and forth between these stages with the caveat that the unit operations cannot be fully configured until the relevant reagents have been defined. Rather than creating all new synthesis programs from scratch, it is also possible to copy an existing synthesis protocol and use that as the starting point. Unit operations refer to those fundamental or building block operations that are employed the radiochemical synthesis process. Examples of unit operations include: ADD (for adding a reagent to a reaction vessel); EVAPORATE (for evaporating the contents of a reaction vessel); TRANSFER (for transferring the contents of one reactor to a next reactor); REACT (seals the reactor vessel to underside of disposable cartridge and heats); PROMPT (pauses sequence run and prompts the user); INSTALL (moves a reactor to the install position for reaction vessel removal and/or installation and prompts the user); TRAPF18 (traps [$^{18}$F]Fluoride on a quaternary methylammonium (QMA) cartridge); ELUTEF18 (uses a reagent to elute [$^{18}$F]Fluoride off a QMA cartridge); MIX (mixes the contents of a reactor by stirring); EXTERNALADD (allows the user to externally add a reagent via tubing); TRANSFERTOHPLC (transfers the contents of the reactor to the HPLC injection loop); MEASURERADIATION (measures the radiation levels observed in the reactor).

Figure 2:
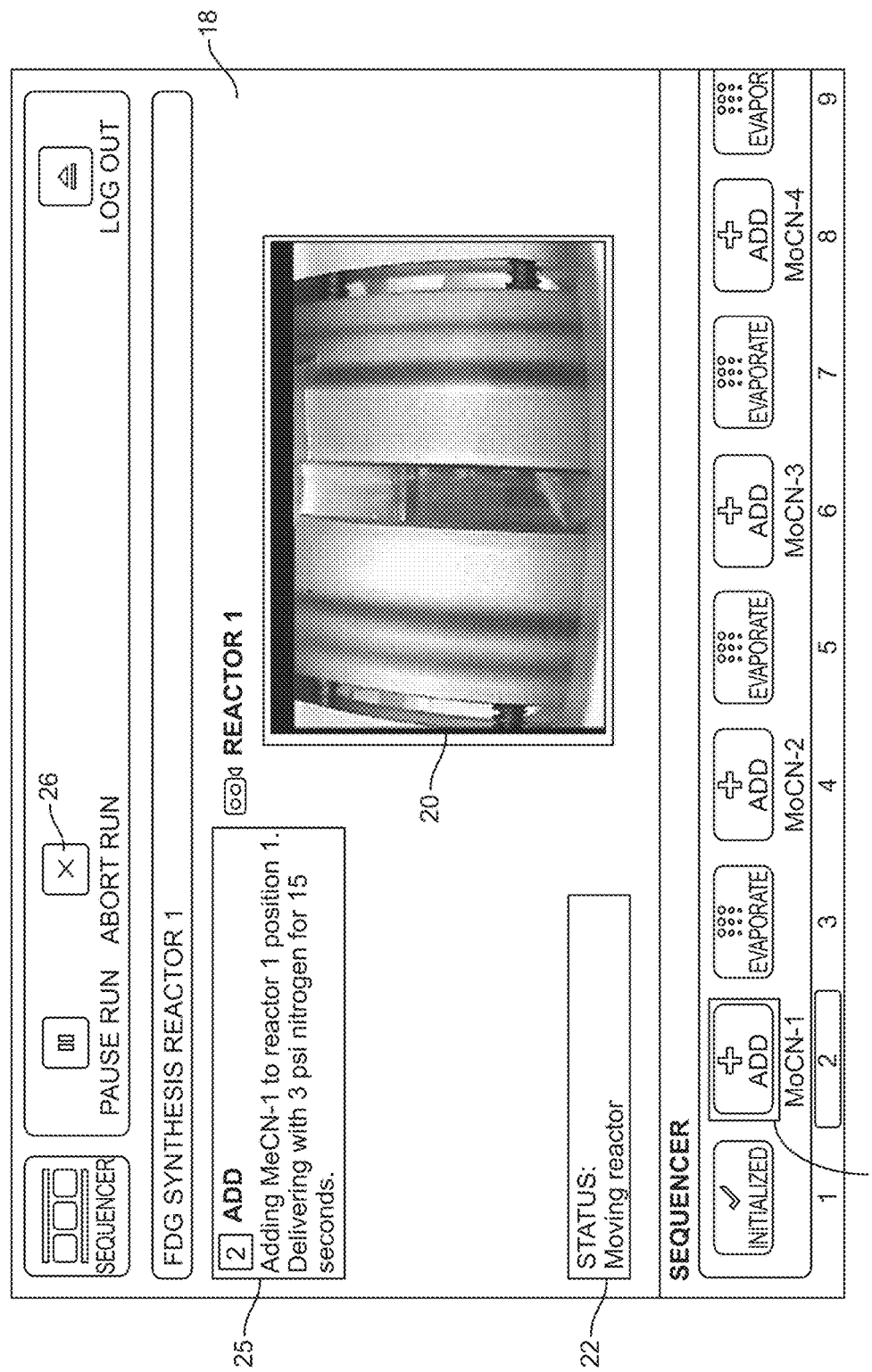
FIG. 2 illustrates an exemplary display that can be displayed on a client device that displays relevant information as to the current unit operation occurring during a synthesis run.

FIG. 2 illustrates an exemplary display 18 that can be displayed on a client device 16 that displays relevant information as to the current unit operation occurring during a synthesis run. In this particular example, [$^{18}$F]FDG is being synthesized in reactor #1. The display includes an active video 20 of rector #1. The system status 22 indicates the current operation being conducted by the synthesizer 12 (e.g., moving reactor #1). A sequencer 24 lists the unit operations in the order in which they are to be performed. Unit operations are performed in a serial fashion moving from one unit operation to the next. The current unit operation 25 is highlighted as illustrated in FIG. 2 (e.g., ADD). The user may be permitted to abort a particular run using abort button 26.

Figure 3:
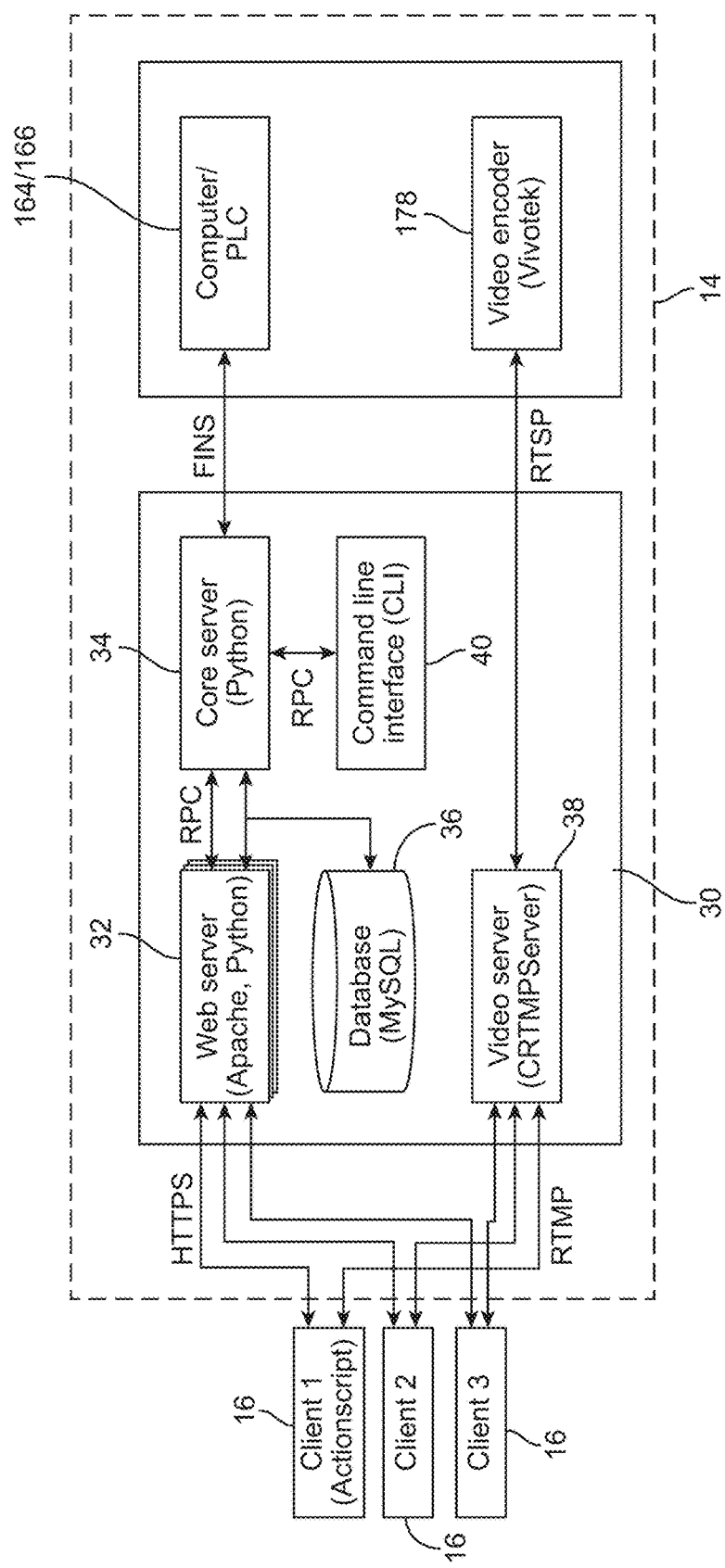
FIG. 3 illustrates an overview of the software architecture used as part of the interface between the client devices and the control system.

FIG. 3 illustrates an overview of the software architecture used as part of the interface between the client devices 16 and the control system 14 according to one embodiment. A server 30 interfaces with the client devices 16 using standard networking protocols to maximize the ability of client-server communication to pass through firewalls. Secure hypertext transfer protocol (HTTPS) is used to transmit all information with the exception of video which is sent using Adobe's real-time messaging protocol (RTMP). The server 30 is responsible for the actual execution of the synthesis program and is designed and built with maximum reliability in mind. To this end, open-source packages with known reliability have been used. Additionally, all information about the state of each client application is stored on the server, so nothing will be lost even if a critical failure (e.g., battery loss and software crash) occurs with the client device 16. The server 30 is driven by the client device 16 but acts independently once the production run has started to make the system resilient to intermittent network connectivity or failures of the client device 16. The server 30 is composed of five main applications. A first main application includes the Web Server 32; An Apache HTTP (Forest Hill, Md., USA) is responsible for all client communication except video. A module written in Python (Wilmington, Del., USA) handles viewing and editing programs and only communicates with the core server for operations related to production runs.

A second application includes a Core Server 34. An application written in Python runs on the Core Server 34 and is responsible for running a program and communicating with a computer 164 or programmable logic controller (PLC) 166 located in the radiosynthesizer 12 that monitors and controls the state of the hardware. The computer 164 or PLC 166 constitutes the third tier of the software. The core server code has been separated from the web server to remove the overhead of program viewing and editing and to insulate it from any failures that might occur while processing client requests. All communications between the web and core servers are accomplished using remote procedure calls.

A third application includes the database (MySQL) server 36. All synthesis programs and user information as well as the complete production run history are stored in a MySQL database (Redwood City, Calif., USA), a widely used, reliable, open-source relational database. A fourth application includes a video server 38. Three live video feeds (one for each reactor) from the respective cameras at each reactor assembly are generated by a hardware encoder within the synthesizer 12 as real-time streaming protocol streams and are converted to the Flash-compatible format RTMP by C++ RTMP Server (e.g., EvoStream (San Diego, Calif., USA) and published for simultaneous consumption by multiple client devices.

A fourth application includes a command line interface 40. A terminal-based command line interface 40 provides a way to monitor the status of all hardware components and offers a mechanism to control the system directly at a low level. Although not needed by or intended for end users, this application is useful for software developers and maintenance technicians.

Returning back to FIG. 1 and to FIGS. 4A-4D the synthesizer 12 includes several main subsystems that are used to carry out the various radiosynthesis operations. A first main subsystem includes a plurality of reactor assemblies 50. The reactor assemblies 50 are used to hold a reactor vial 52 (e.g., 5 mL glass V-vial) within a central aperture 54. Each reactor vial 52 is configured to hold reagents, precursors, and products generated during the radiosynthesis operations. In the illustrated embodiments there are three such reactor assemblies 50 (e.g., reactor #1, reactor #2, and reactor #3 in FIG. 1). While three such reactor assemblies 50 are illustrated, there could be more or less depending on the particular synthesis. Further, even in a configuration with three (3) reactor assemblies such as that illustrated only one or two reactor assemblies 50 could be utilized in any particular run. In some embodiments, the reactor vial 52 is open at the upper lip or rim. In other embodiments, however, the reactor vial 52 may be sealed with a septum which is penetrated by needles located on the underside of cassettes 80.

Each reactor assembly 50 includes a plurality of spring-biased heating assemblies 56. Three such spring-biased heating assemblies 56 are shown in the illustrated embodiments. The spring-biased heating assemblies 56 use respective springs to press the heating assembly radially inward against the surface of the reactor vial 52 when placed therein. In this regard, the spring-biased heating assemblies 56 act as a three-segment spring-loaded "chuck." Each spring-biased heating assembly 56 presses firmly against the reactor vial 52 to ensure excellent thermal contact and thus efficient heat exchange between the reactor assembly 50 and the reactor vial 52. Each spring-biased heating assembly 56 includes a 100 W cartridge heater 58 (CIR-1021-120V-100 W-ST-A, Valin; San Jose, Calif., USA) and a K-type thermocouple 60 (HTTC72-K-116U-1.25-UNGR, Omega Engineering; Stamford, Conn., USA) for individual feedback control of the reactor assembly temperature up to 185° C. Since a very similar temperature response was typically observed in all three segments, the reactor assembly temperature at any given moment is considered equal to the average of the three temperature readings from the thermocouples. Active liquid cooling is achieved by pumping room temperature coolant (propylene/ethylene glycol and water mixture) through cooling channels 62 in all three reactors in series by a liquid pump (8030-863-236, Steam Brite; San Antonio, Tex., USA) and then through a radiator 174 with three 140 mm fans (HX-CU1403V, Frozen CPU; East Rochester, N.Y., USA) (pump and radiator illustrated in FIGS. 8 and 9).

The reactor assembly 50 further includes a camera 64 (PC213XS, Super Circuits; Austin, Tex., USA) affixed to a mount 66. The camera 64 was mounted behind the reactor assembly 50, which is helpful for monitoring liquid levels during evaporations, to observe visual cues for reaction progression, to confirm reagent additions and transfers, and for visual inspection of the eluate post purification. The camera 64 is oriented relative to the spring-biased heating assembly 56 such that it has a clear view of the reactor vial 52. In one embodiment, as best seen in FIG. 4D, portions of the spring-biased heating assembly 56 may have optional graduation marks 57 in the form of collets to gauge liquid volume in the reactor vial 52 (visible to camera 64).

Figure 4D:
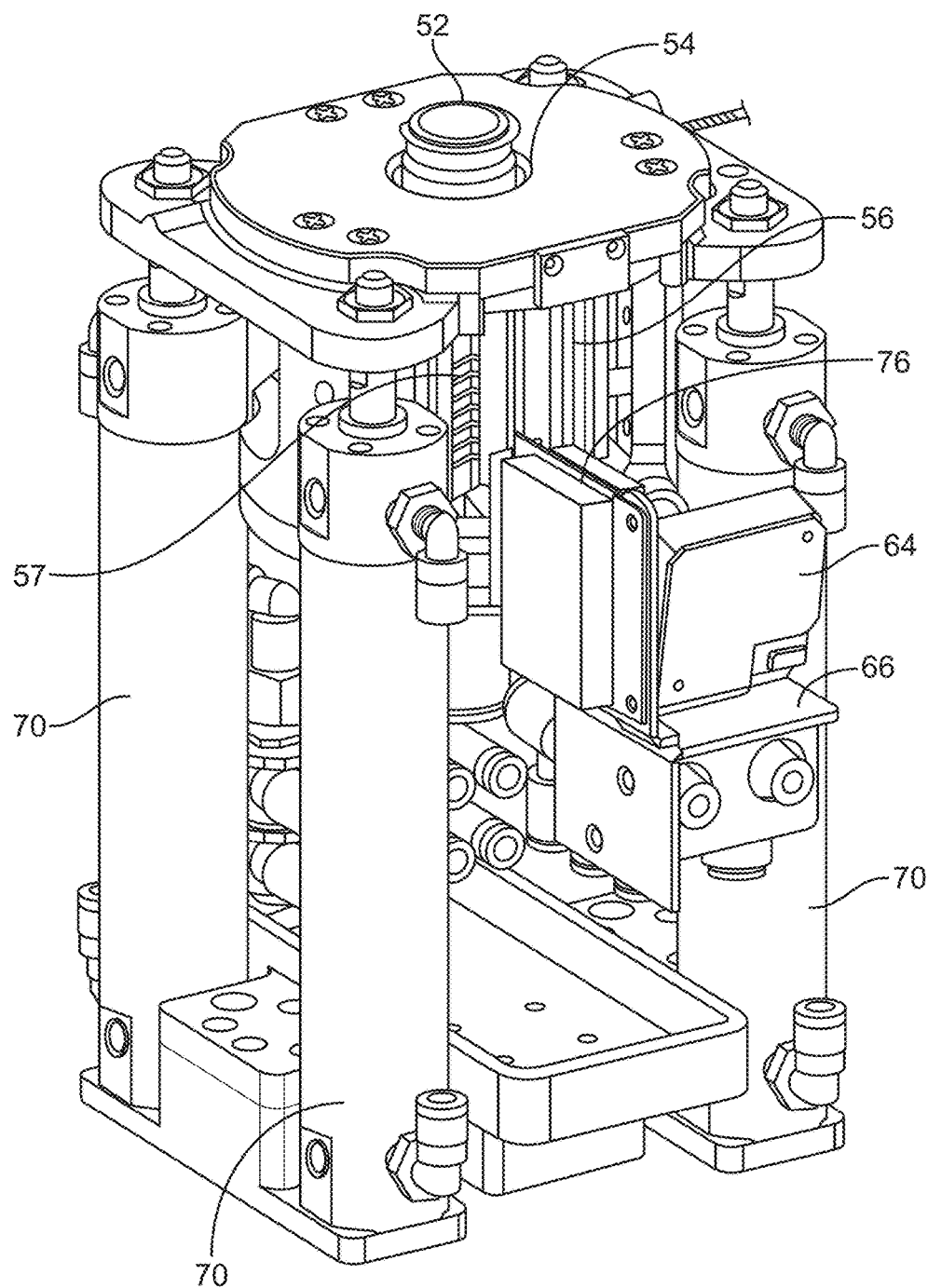
FIG. 4D illustrates a perspective view of a reactor assembly according to another embodiment illustrating the position of a radiation sensor.

Still referring to FIGS. 4A, 4B, and 4D, each reactor assembly 50 includes a plurality of vertically-oriented actuators 70 that are mounted at one end (bottom) to a horizontally-oriented actuator 72. The opposing end of the vertically-oriented actuators are mounted to the reactor assembly 50 that that the entire reactor assembly 50 can be raised and lowered depending on actuator of the vertically-oriented actuators 70. In one aspect, there are four (4) such vertically-oriented actuators 70 with each actuator being a pneumatic actuator that is coupled to a source of valved, pressurized gas. When pressurized gas is delivered to the vertically-oriented actuators 70 the reactor assembly 50 is raised in the vertical direction so as to place the reactor vial 52 therein in a sealed configuration against gaskets 90 positioned on the bottom surface of disposable cassettes positioned directly above each reactor assembly 50 (described in more detail below). Also, as described above, the horizontally-oriented actuator 72 is able to move the reactor assembly 50 in the lateral direction. This two axis movement by the reactor assembly 50 permits the reactor vial 52 to be selectively and dynamically configured for different unit operations based on the particular gasket 90 that it interfaces with on the underside of the disposable cassette (described below).

For example, in one position, the gasket 90 is un-sealed within internal plumbing or fluid paths within a disposable cassette 80 configured to deliver reagents to the reactor vial 52 within the reactor assembly 50. In another position, the gasket 90 is sealed, allowing for a reaction under sealed conditions. Permanent tubing and valve connections to the reaction vessel are the root cause of the reaction pressure limitations of most synthesizers. The ability to move the reactor vial 52 to a dedicated sealed reaction position eliminates these limitations and enables compatibility with higher pressures. To ensure reliable operation, the position of the reactor assembly 50 is monitored via feedback from the linear actuator and the raised or lowered state is detected with Hall effect sensors (D-M9NWL, SMC Corporation; Noblesville, Ind., USA).

The horizontally-oriented actuators 72 which move, respectively, the reactor assemblies 50 in the y-axis may include linear servo motors (RCP3-SA3R-I-28P-4-200-P1-P-ML, IAI America Inc.) driven by linear servo motor controllers (RACON-5, IAI America Inc.). The y-axis movement of the horizontally-oriented actuators 72 is aligned with the direction of the gaskets aligned along the bottom of the disposable cassette (discussed below). The reactor assemblies 50 each include magnet mounted on a DC motor 67 as seen in FIG. 4B (803-313-5858, KALEJA Elektronik GmbH; Alfdorf, Germany) which interacts with a removable magnetic star bar located inside the reaction vial 52, causing the magnetic stir bar to rotate for mixing operations. The reactor assemblies 50 each optionally include a radiation sensor 74 that is mounted adjacent to the camera 64. The radiation sensor 74 may be mounted to the mount 66. An optional radiation sensor (not shown) may also be placed adjacent to a purification cartridge 132.

With reference now to FIGS. 1 and 5A-5D, the synthesizer 12 includes a plurality of disposable cassettes 80 that can be manually loaded into the synthesizer 12 and affixed into place into respective bays 82 located vertically above each reactor assembly 50. Thus, in a "three-pot" reactor assembly 50 configuration, there are three bays 82 with each bay holding an individual cassette 80. The cassettes 80 store reagents in sealed vials 84 on an upper surface 86 in one of a plurality of vial storage positions 88, act as the primary fluid path for both reagents and gas flow, and have a rubber or silicon gasket 90 (seen in FIG. 5C) affixed to a lower surface 92 of the cassette 80 for sealing the top or lip of the reaction vials 52. The cassettes 80 accelerate setup and eliminate the need for cleaning, thus facilitating the transition from tracer development to routine production. The cassettes 80 can be made from molded polyurethane, tubing, chemically-inert three-way stopcock valves 102 (EW-31200-80, Cole-Parmer; Vernon Hills, Ill., USA), and a custom PTFE-coated silicone gasket 90 (Specialty Silicone Products, Inc.; Ballston Spa, N.Y., USA; and Cannon Gasket; Upland, Calif., USA) against which the reactor vial 52 is sealed.

The cassettes 80 are manually loaded into each bay 82 using respective rails 94 that interface with tabs 95 located on the cassettes 80. Once the cassettes 80 are slid into the bays 82 sufficiently they drop onto a support plate 96 that holds the cassettes 80. Each cassette 80 contains a plurality of alignment pegs 98 located in the bottom surface that engage with corresponding holes (not shown) in the support plate 96. The cassettes 80 are also held into position with adapters that are secured to three valve actuators 100 that engage with three corresponding stop cock valves 102 that are accessible via the lower surface 92 of the cassette 80. The cassettes 80 can be further held in place using fasteners 103 which may take the form of rotatable clips or knobs (as seen in FIG. 5A).

Figure 5B:
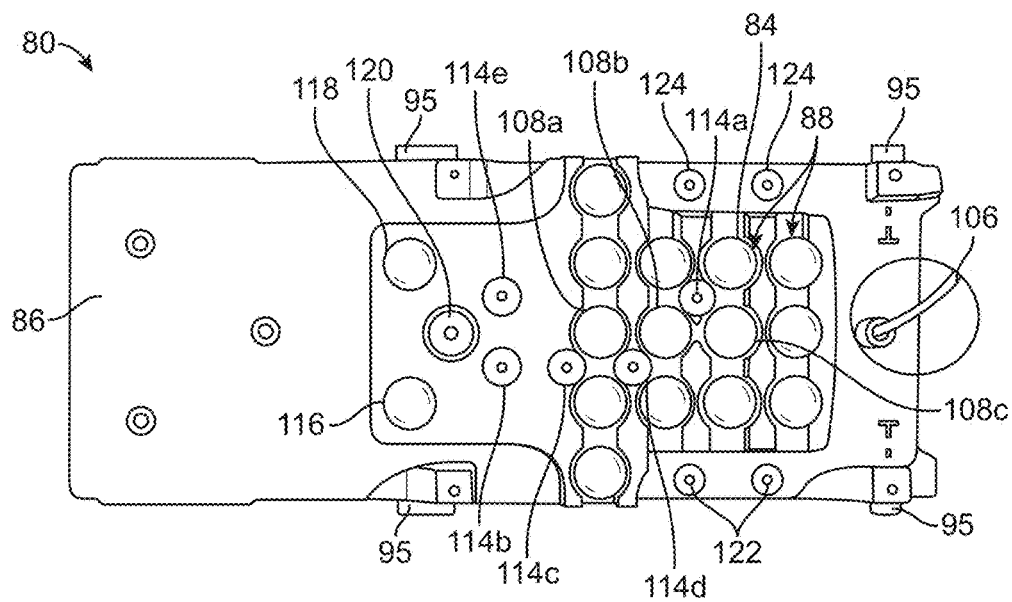
FIG. 5B illustrates a top down view of a disposable cassette according to one embodiment.
Figure 5C:
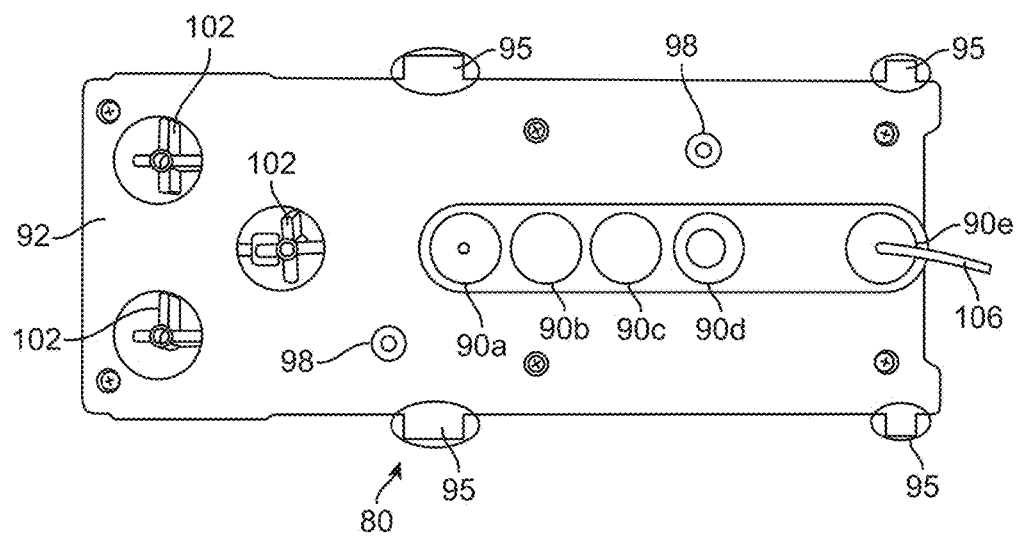
FIG. 5C illustrates a bottom up view of a disposable cassette according to one embodiment.
Figure 5D:
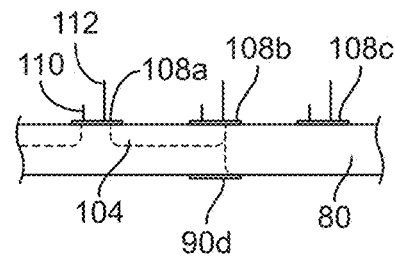
FIG. 5D illustrates a cross-sectional view of disposable cassette.

FIG. 5C illustrates a view of the bottom or lower surface 92 of the cassette 80. The three stop cock valves 102 are illustrated. As noted above, the stop cock valves 102 can be rotated using a valve actuator 100. The valve actuator 100 is preferably a rotary pneumatic actuator that can turn between two states (CRB2BW20-1805, SMC Corporation). Also illustrated are a series of gaskets 90a, 90b, 90c, 90d, and 90e. Gaskets 90a, 90b, 90c, 90d, and 90e are formed from a rubber or silicone material and are dimensioned to encompass the full diameter of the upper lid or rim of the reactor vial 52. Gasket 90a is un-sealed in that an aperture is located in the gasket 90a and is in communication with an internal fluid path 104 of the cassette 80 (internal flow path 104 illustrated in FIG. 5D and FIGS. 6B-6G). Gasket 90a is used for the EVAPORATE unit process whereby vacuum is pulled in conjunction with flow of an inert gas. Gasket 90b and gasket 90c are sealed gaskets that do not have any aperture or other access into to the internal fluid path 104 of the cassette 80. These gaskets 90b, 90c are used for the REACT unit process whereby high pressures can be formed and maintained within the reactor vial 52 when the reactor assemblies are positioned below the same and actuated in the elevated position. Gasket 90d is un-sealed in that an aperture is located in the gasket 90d and is communication with an internal fluid path 104 within the cassette 80. Gasket 90e is an un-sealed gasket that includes a dip tube 106 that extends through the cassette 80 and is used extract fluid from a reactor vial 52. Fluid can be extracted by injecting inert gas into the reactor vial 52 through a needle or aperture passing through gasket 90e to push fluid into the dip tube 106. Fluid can then be transferred via the dip tube 106 to another cassette 80, for example. As noted above, in some embodiments, the lower surface 92 of the cassette 80 has needles or the like to penetrate sealed reactor vials 52. Such may be the case when the reagents used in the automated synthesizer 10 are air or moisture sensitive.

FIG. 5B illustrates top view of the cassette 80 illustrating the upper surface 86. The upper surface 86 includes a plurality of vial storage positions 88 that are used to store sealed storage vials 84 that contain reagent therein. The storage vials 84 are crimped septum-cap vials (e.g., 13 mm vials with maximum volume of 3 mL). Eleven (11) such storage vials 84 are illustrated being stored in the upside down configuration in the cassette 80 although more or less could be used. The cassette 80 also includes a plurality of reagent addition positions 108a, 108b, 108c. The reagent addition positions 108a, 108b, 108c are used in the ADD unit operation to add reagents to one of the reactor vials 52. Each reagent addition position 108a, 108b, 108c includes two upward pointing needles 110, 112 that are used to pierce the septa in the storage vials 84 for fluid delivery to the internal fluid path 104 of the cassette 80 (e.g., stainless steel needles (Vita Needle; Needham, Mass., USA)). A shorter needle 110 in each addition position 108a, 108b, 108c is used for fluid delivery. The other needle 112, which is longer, connects to an inert gas port 114 on top of the cassette 80 which allows pressurization of the vial by the gas manifold 152 (discussed in more detail below). In the two reagent addition positions 108a, 108b, the fluid delivery needles 110, 112 output directly to the underside of the cassette 80 where the reaction vial 52 is sealed for reagent addition. The fluid delivery needle in the third position 108c (for eluent addition) is connected via an internal fluid path 104 to a stopcock valve 102.

Still referring to FIG. 5B, the cassette 80 includes a number of inlet gas ports 114a, 114b, 114c, 114d, 114e. Gas inlet port 114a is connected via an internal fluid path 104 to the dip tube 106. The gas inlet ports 114b, 114c, 114d are each respectively coupled to reagent additions positions 108a, 108b, 108c. Thus, each reagent addition position 108a, 108b, 108c has a dedicated gas inlet port 114b, 114c, 114d. Gas inlet port 114e is used is used to supply a stream of inert gas through the reactor vial when it is in the evaporate position. The cassette 80 further includes a cartridge waste vial location 116 that holds a vial that receives waste. The cassette 80 also includes a recovery vial location 118 that holds a vial that receives recovered [$^{18}$O]H$_2$O. The upper surface 86 of the cassette 80 further includes a vacuum port 120 that selectively interfaces with a gas manifold 152 on the reagent and gas handling robot 140 that is coupled to a source of vacuum. In this regard, vacuum can be supplied to the gasket 90a for the EVAPORATE unit operation.

The cassette 80 further includes inlet ports 122 that are used delivery fluid into internal fluid path 104 of the cassette 80. Tubing is used to connect to the inlet ports 122 and can be used to deliver fluids into the cassette 80 (and ultimately the reactor vial 52) from an external source outside the cassette 80. Alternatively, the output of one cassette 80 may be input to another cassette 80 using the inlet ports 122. Likewise, outlet ports 124 are provided on the cassette 80 that are configured to connect to tubing. The outlet ports 124 may output a fluid that is collected at a collection vial 126 (FIG. 6A) for the final product. Alternatively, the outlet ports 124 can be used to transport an intermediate or precursor from one cassette 80 to another cassette 80. For example, tubing or other conduit may be connected between the outlet port 124 of a first cassette 80 and terminate at the inlet port 122 of another, separate cassette 80.

Figure 6A:
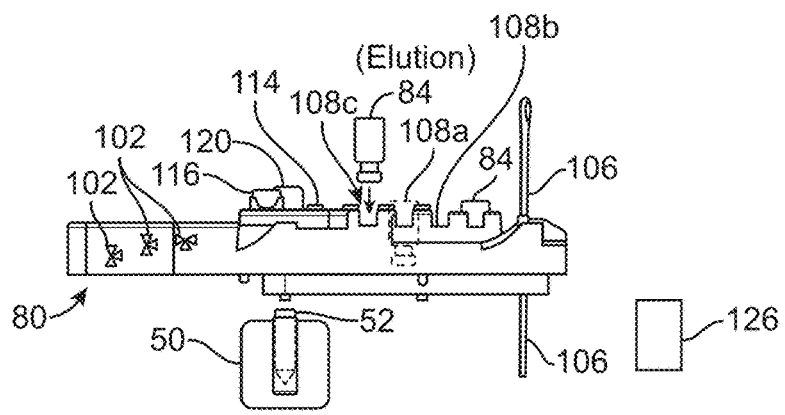
FIG. 6A illustrates a side profile schematic of the disposable cassette.
Figure 6B:
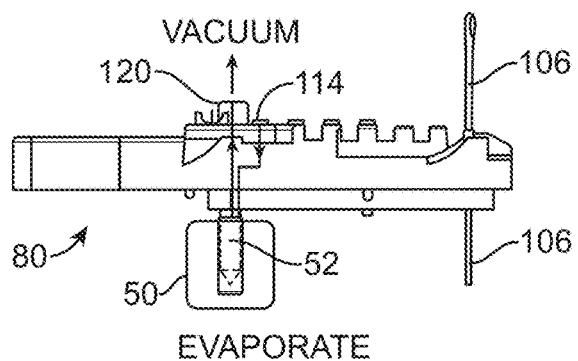
FIG. 6B is a schematic drawing showing the cassette fluid path for EVAPORATE. Gas supplier provides vacuum and inert gas flow while reactor is heated.
Figure 6C:
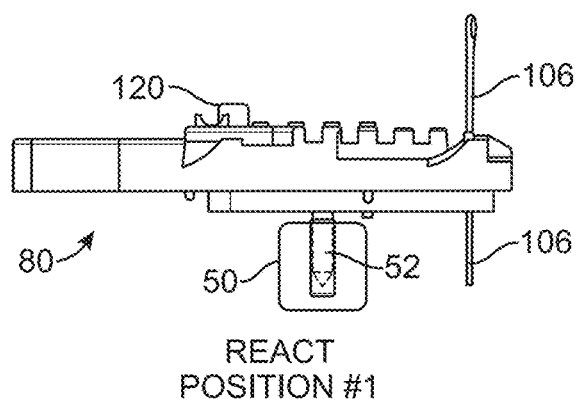
FIG. 6C is a schematic drawing showing the cassette fluid path for REACTION; Reaction 1. First fully-sealed reaction position.
Figure 6D:
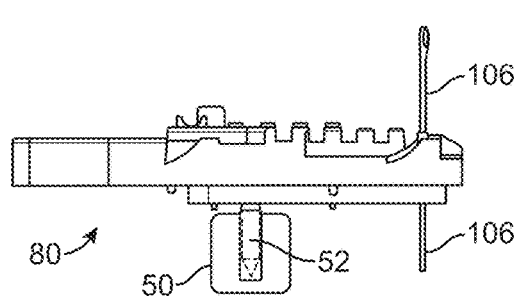
FIG. 6D is a schematic drawing showing the cassette fluid path for REACTION; Reaction 2. Second fully-sealed reaction position.

FIG. 6A illustrates a side profile schematic representation of the cassette 80. The three (3) stopcock valves 102 can be seen. A reactor assembly 50 containing a reactor vial 52 is illustrated below gasket 90a used for the EVAPORATE unit process. FIG. 6B illustrates a side profile view of the cassette 80 illustrating the gas flow path 128 and the vacuum flow path 130. The reactor assembly 50 is in the raised position so as to place the reactor vial 52 against the gasket 90a for the EVAPORATE unit process to take place. FIGS. 6C and 6D illustrate the reactor assembly 50 in react positions #1 and #2 for REACT unit processes to take place. FIG. 6C illustrates the reactor assembly 50 in the raised position so as to place the lip or rim of the reactor vial 52 against the sealed gasket 90b. FIG. 6C illustrates the reactor assembly 50 in the raised position so as to place the lip or rim of the reactor vial 52 against the sealed gasket 90c. In this position, high temperature and high pressure reactions can take place within the reactor vial 52.

Figure 6E:
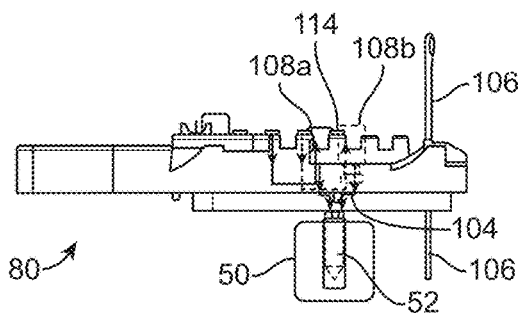
FIG. 6E is a schematic drawing showing the cassette fluid path for ADDITION. Vial gripper presses a reagent vial into one of two addition positions where two needles pierce the vial's septum; one needle allows inert gas flow from the gas supplier through the inert gas port and the other needle allows the reagent to flow into the reaction vessel.
Figure 6F:
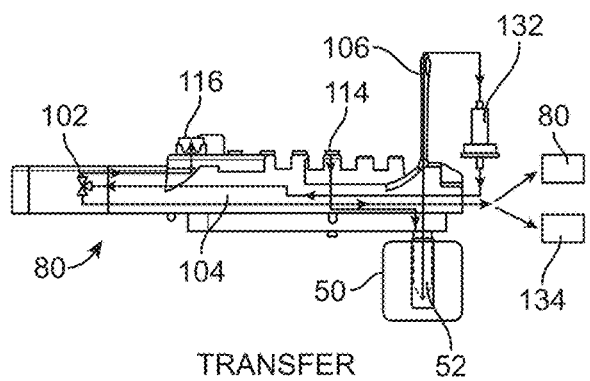
FIG. 6F is a schematic drawing showing the cassette fluid path for TRANSFER. The contents of one reaction vessel are transferred to another cassette, the HPLC valve, or to a purification cartridge.

FIG. 6E illustrates a configuration whereby the reactor assembly 50 and the reactor vial 52 contained therein are placed in the addition position for the ADD unit operation. Here, the reactor assembly 50 is in the raised position so as to place the lip or rim of the reactor vial 52 against the un-sealed gasket 90d. Reagents can then be actively transported into the reactor vial 52 via the internal fluid path 104 by flowing inert gas through inert gas port 114 to displace the reagent from the storage vial 84 and into reactor vial 52. FIG. 6F illustrates configuration whereby the reactor assembly 50 and the reactor vial 52 contained therein are placed in transfer position for the TRANSFER or TRANSFER-TOHPLC unit operations. The reactor assembly 50 is in the raised position so as to place the lip or rim of the reactor vial 52 against the un-sealed gasket 90e. The dip tube 106 is used to transfer the fluid contained within the reactor vial 52 to another location. Such a location could include another cassette 80, a purification cartridge 132 as illustrated, or a HPLC injection valve 134, or a collection vial 126 to store a final product. FIG. 6F illustrates a purification cartridge 132 that is coupled to the output of the dip tube 106.

The purification cartridge 132 is installed between the dip tube 106 (for removal of crude product from the reaction vial 52) and the tube leading to the stopcock valve 102. The outputs of the stopcock valve 102 are connected to a built-in waste vial 116 (trapping, washing) or an external output line via outlet port 124 (release). Cartridges 132 can optionally be mounted on clips near the front of the cassettes 80 for convenience. Alternatively, the cartridges 132 can be mounted on a support structure of the synthesizer 12 separate from the cassettes 80.

Figure 6G:
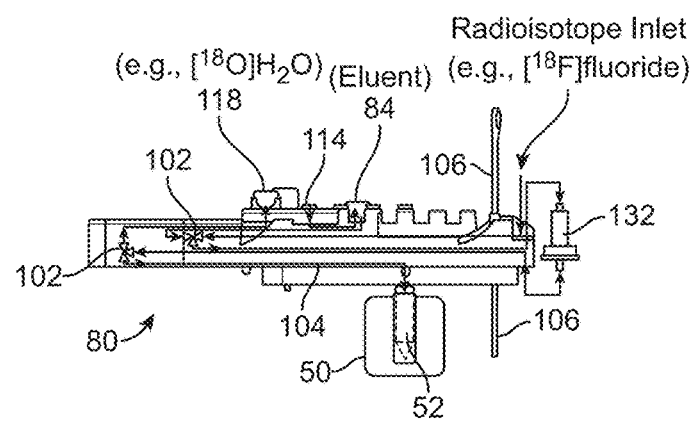
FIG. 6G is a schematic drawing showing the cassette fluid path for Radioisotope handling. [$^{18}$F]fluoride trap and release is performed using two of the built in stopcock valves.

FIG. 6G illustrates a configuration used for radioisotope handling. In this configuration, [$^{18}$F]fluoride trap and release can be done using two of the built in stopcock valves 102. The reactor assembly 50 and reactor vial 52 are raised to contact the upper lip or rim of the reactor vial to the un-sealed gasket 90d. Radioisotope such as [$^{18}$F]fluoride obtained from a cyclotron or vial is input into the cassette 80 via the inlet tubing port 122. In nucleophilic fluorine-18 radiochemistry, [$^{18}$F]fluoride is trapped on a strong anion exchange resin such as quaternary methylammonium (QMA) resin for purification and recovery of [$^{18}$O]H$_2$O and released in a solution with lower water content to reduce the time needed for drying. This is accomplished using a cassette 80 that is coupled to a QMA cartridge 132 via Luer fittings between tubes coming from the cassette 80. If an external vial is used, an external inert gas delivery line coupled to an inert gas port 114 is available to pressurize the vial for delivery on demand. Alternatively, the gas delivery system of the cyclotron can be used to directly push the [$^{18}$F]fluoride into the system. In FIG. 6G, this flow is valved using stopcock valve 102 to a purification the QMA cartridge 132. During trapping, the [$^{18}$F]fluoride source solution flows through the QMA cartridge 132 where [$^{18}$F] fluoride is retained and the carrier [$^{18}$O]H$_2$O, then flows into the recovery vial 118 in the cassette 80. During elution, stopcock valve 102 positions are switched and the gas handling robot drives the eluent from the eluent addition position of the cassette 80 through the QMA cartridge 132 and into the reactor vial 52. Multiple elutions can be performed to increase efficiency of [$^{18}$F]fluoride collection. PEEK tubing can be used for all fluid paths involving [$^{18}$F]fluoride to maximize specific activity. For other radioisotopes, a cartridge 80 may not be necessary and can be bypassed. Radioisotopes may be added to any of the three reactors independently.

Figure 7A:
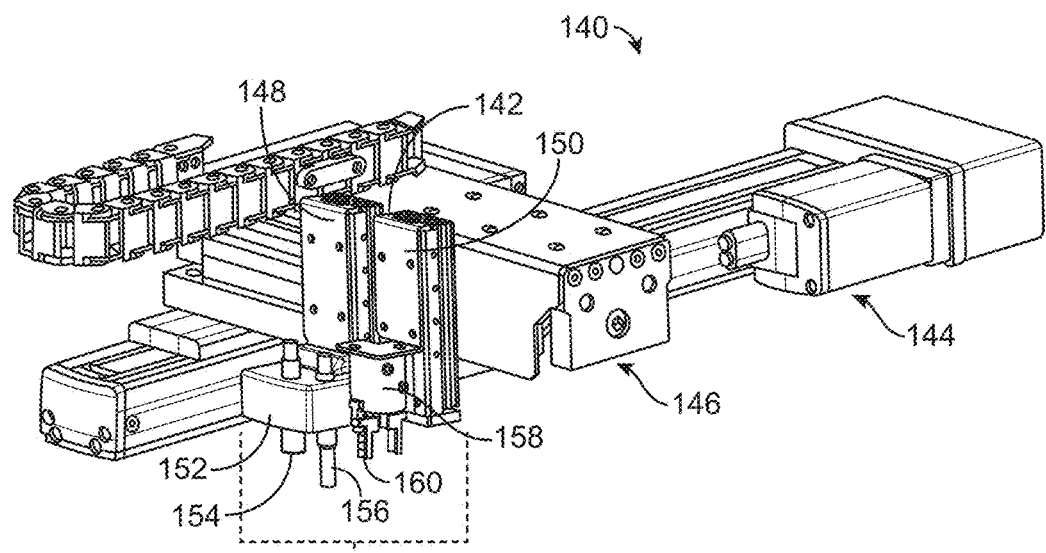
FIG. 7A illustrates a perspective view of the reagent and gas handling robot.
Figure 7B:
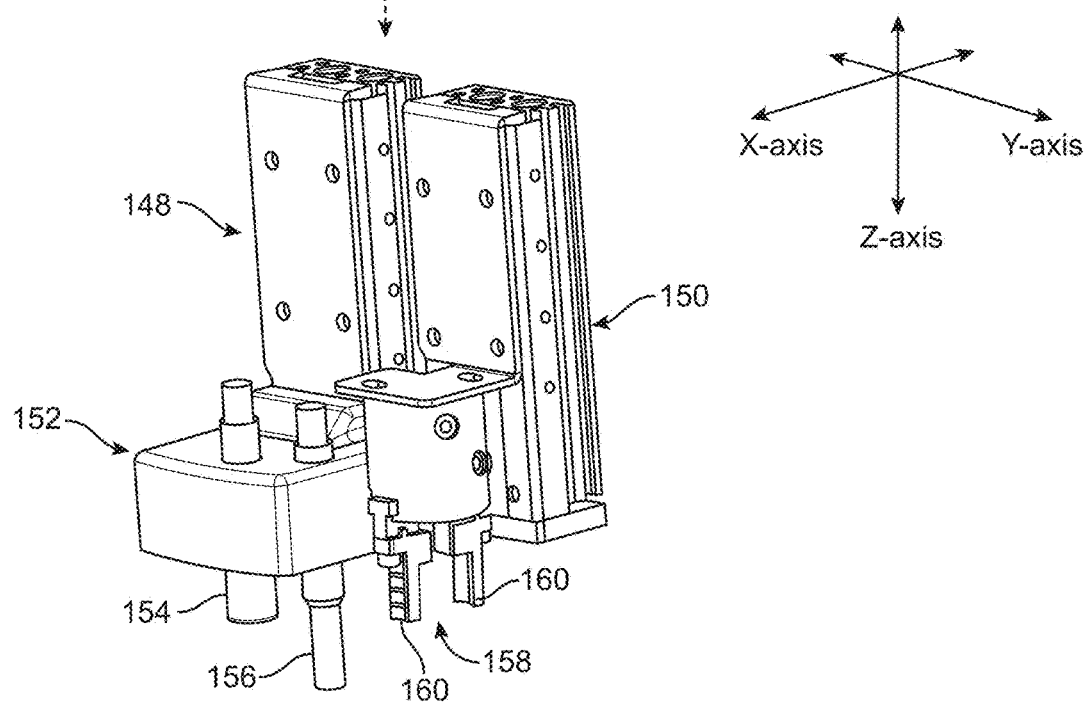
FIG. 7B illustrates a perspective, close up view of the z-axis actuators for the gas manifold and vial gripper.

FIGS. 7A and 7B illustrate the reagent and gas handling robot 140. The reagent and gas handling robot 140 is disposed above the cassettes 80 and the reactor assemblies 50. The purpose of the reagent and gas handling robot 140 is to move the sealed storage vials 84 containing reagents and other materials from the storage positions 88 in the cassette 80 to the addition positions and also dynamically provide vacuum and inert gas delivery via vacuum port 120 and inert gas ports 114 on the cassette 80. The reagent and gas handling robot 140 is a 3-axis Cartesian robot that is able to move storage vials 84 with reagents on demand. This preserves the reagent 'freshness' until the last possible moment. In other systems, sensitive reagents may be compromised because the reagents are placed onto needles during setup (prior to starting the synthesis), or are transferred during setup from their original vials into reservoirs that are a permanent part of the synthesizer 12. The reagent and gas handling robot 140 approach helps to eliminate the need to reconfigure the plumbing for different synthesis protocols (i.e., the choice of which reagents are "connected"

to which reaction vial 52 is made not by the plumbing configuration but is simply specified in software). The reagent and gas handling robot 140 is also used for forming connections of inert gas and vacuum to the inert gas port 114 and vacuum port 120, respectively. The inert gas is used to drive fluid movement and assist with evaporations. Vacuum is applied via the vacuum port 120 to remove vapor during the EVAPORATION unit process.

The reagent and gas handling robot 140 includes a head portion 142 that moves in the x and y directions. An x-axis motion actuator 144 moves the head portion 142 in the x direction while a y-axis motion actuator 146 moves the head portion 142 in the y direction. Attached to the head portion 142 are two respective z-axis actuators 148, 150. The first z-axis actuator 148 includes a pneumatic actuator that moves a gas manifold 152 in the z direction. The gas manifold 152 includes a vacuum port 154 and an inert gas port 156. Respective tubes (not shown) connect the vacuum port 154 to a source of vacuum and the inert gas port 156 to a source of inert gas (e.g., Nitrogen, not illustrated). The vacuum port 154 is dimensioned to fit within the vacuum port 120 located on the cassette 80. The inert gas port 156 is dimensioned to fit within the inert gas port 114. The second z-axis actuator 150 is coupled to a vial gripper 158. The vial gripper 158 includes a plurality of fingers 160 that can be selectively open or closed to engage with the storage vials 84. Storage vials 84 can thus be picked up and moved by the reagent and gas handling robot 140.

The use of Hall-effect sensors as feedback devices on the z-axis actuators 148, 150 and the vial gripper 158 prevent the system from adding storage vials 84 that may be missing, or moving the reagent and gas handling robot 140 if the vial gripper 158 and gas manifold 152 are not in their raised, clearance positions. An in-line check valve (CI-5C, Bio Chem Fluidics; Boonton, N.J., USA) is installed on the inert gas line close to the delivery point to eliminate back flow of vapor. A cold-trap (CG451501, Chemglass; Vineland, N.J., USA), cooled in a small dewar (10-195A, Fisher Scientific; Pittsburgh, Pa., USA), typically with a mixture of dry ice and methanol, can be installed in-line between the vacuum port and the integrated vacuum pump (VP0140-V1006-D2-0511, Medo USA Inc.; Roselle, Ill., USA) and digital vacuum gauge (ZSE30-N7L, SMC Corporation).

A source of inert gas is reduced from >60 psig down to two different pressures by two analog pressure regulators (ITV1030-31N2L4-Q, SMC Corporation), respectively. One pressure line drives the pneumatic actuators and is typically set at 60 psig, but can be dynamically adjusted by modifications of the software as needed; the other pressure line drives gas flow for liquid transfers and evaporation (typically 3-15 psig). These two lines are distributed to actuators and the gas manifold 152 through solenoid valve banks (not shown) located in the synthesizer 12. The higher-pressure line is used to: raise and lower the reactor assembly 50 and reactor vial 52 against the cassettes 80 using pneumatic cylinders 70 (NCDGBN20-0300, SMC Corporation); turn the stopcock valves 102 via the rotary pneumatic actuators (CRB2BW20-1805, SMC Corporation); raise and lower the two z-axis actuators 148, 150 (MXS8-50, SMC Corporation) for the vial gripper 158 and gas manifold 152; and open and close the vial gripper 158 (MHS2-16D, SMC Corporation). The lower-pressure line, for example, feeds into the gas manifold 152 and functions to seal the gas inlet gaskets on top of the cassettes 80, and an external line that can be used to transfer [$^{18}$F]fluoride from a source vial into the anion exchange cartridge on the cassette 80.

Figure 8:
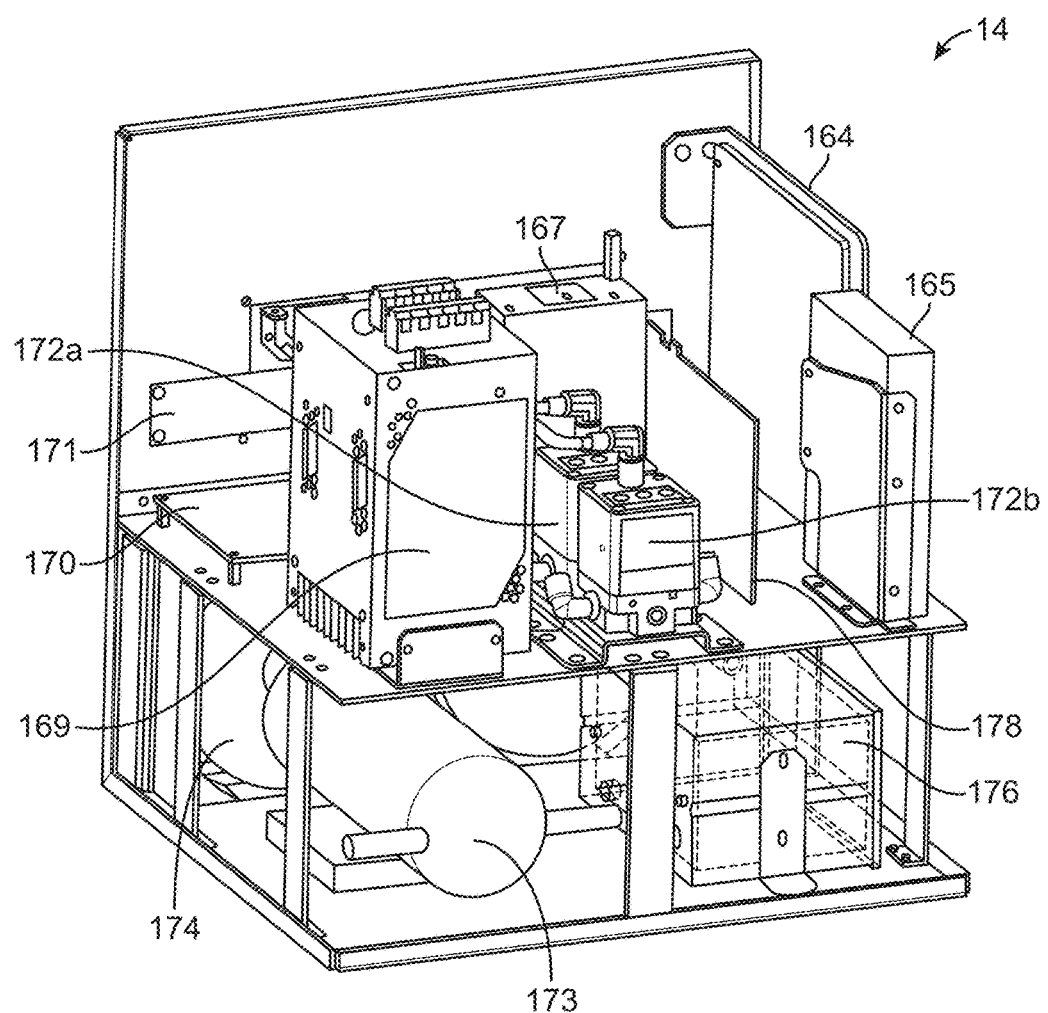
FIG. 8 illustrates a control unit according to one embodiment.

Referring to FIG. 8, supporting electronics, pneumatics, and cooling system are enclosed in a separate control system 14. The control system 14 includes an embedded computer 164 that interfaces via ethernet to the client device 16 as well as a microcontroller 180 located in the synthesizer 12. A storage device 165 such as a hard drive is contained in the control system 14 and connects to the embedded computer 164. A power supply 167 for the embedded computer 164 supplies power to the embedded computer 164. A DC power supply 169 is contained in the control system 14 for powering, for example, a microcontroller 170 which is formed on a PCB. An input/output (I/O) panel 171 provides for various cables running between the synthesizer 12 and the control system 14. The control system 14 further includes a coolant pump 173 that is coupled to a radiator 174 for heat exchange and a reservoir 176 for coolant storage. Two pressure regulators 172a, 172b are located within the control system 14 and regulate the pressure of inert gas and compressed air, respectively. A video encoder 178 is contained in the control system 14 and receives video feed from cameras 64

As an alternative to the embedded computer 164, a programmable logic controller (PLC) 166 could be used as illustrated in FIG. 3 (PLC, CJ2M-CPU31, Omron; Kyoto, Japan The PLC accomplishes this through several expansion modules (CJ1 W-DRM21, CJ1 W-AD081-V1, CJ1 W-ID261, CJ1 W-DA08V, CJ1 W-OD261, CJ1 W-TC001, Omron). In this embodiment, five motor controllers are connected to a RoboNET network controller 182 gateway unit (RGW-DV, IAI America Inc.; Torrance, Calif., USA) located in the synthesizer 12 which is in turn controlled by the embedded computer 164 or PLC 166. Two of these are pulse motor controllers (RPCON-42P, IAI America Inc.) that drive the x- and y-axes of the reagent and gas handling robot 140, a 350 mm and 100 mm stroke two-axis linear servo motor (actuators 144, 146) (RCP2-557R-I-42P-12-350-P1-007L-ML-SP, RCP3-TA7R-I-42P-6-100-P1-N-ML, IAI America Inc.). The other three controllers are linear servo motor controllers (RACON-5, IAI America Inc.) driving the linear servo motor (actuator 72) (RCP3-SA3R-I-28P-4-200-P1-P-ML, IAI America Inc.) for y-axis motion of each reactor assembly 50.

The control system 14, in one embodiment, also houses a number of other components including, but not limited to, the solid state relays (G6B-4BNDDC12, Omron) to switch the heaters on and off for reactor assembly temperature control, the cooling system (coolant pump, reservoir, and radiator fans), a video encoder 178 (VS8401, Vivotek; San Jose, Calif., USA) to encode the analog signals from the reactor cameras 64 into video streams available to the Linux server via Ethernet, and an electronically-controlled HPLC injection valve 134 (MHP7900-500-1, Rheodyne; Rohnert Park, Calif., USA) connected to a separate semi-preparative HPLC system (not shown). Loading of the HPLC loop can be performed manually or automatically.

Figure 9:
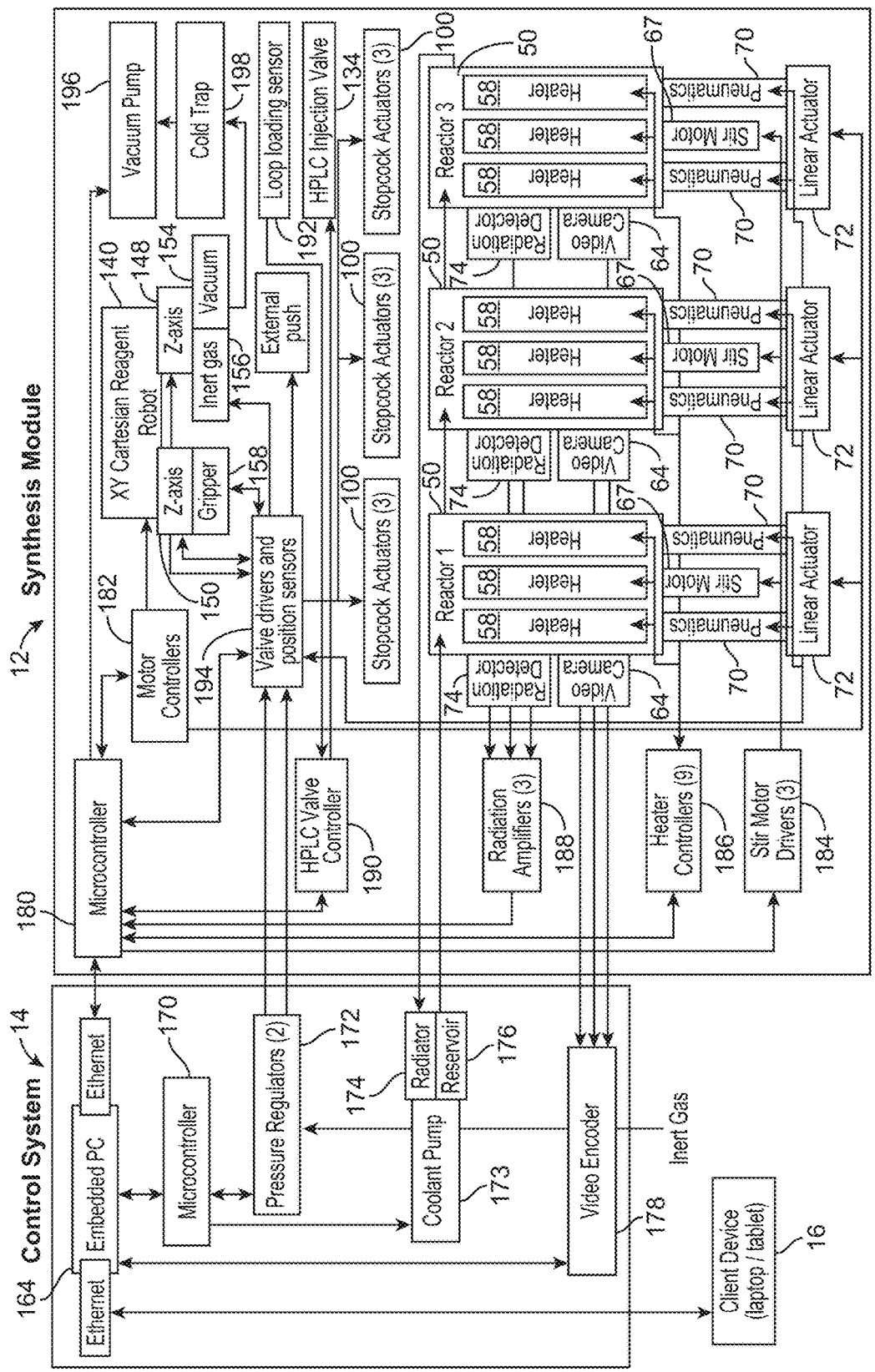
FIG. 9 illustrates the control schematic for the control system for the automated synthesizer.

FIG. 9 illustrates the control schematic for how the control system 14 interfaces with various aspects of the synthesizer 12 according to another embodiment. The control system 14 includes an embedded computer 164 (as opposed to PLC) that communicates via ethernet to a client device 16. A microcontroller 170 is located within the control system 12 that controls pressure regulators 172 and coolant pump 173. The coolant pump 173 has a radiator 174 and a reservoir 176 that circulates coolant to the reactor assemblies 50. The embedded computer 164 also interfaces with a video encoder 178 is coupled to each camera 64. Still referring to FIG. 9, the synthesizer 12 includes its own microcontroller 180 that interfaces with motor controllers 182 (as described above). The motor controllers 182 drive the reagent and gas handling robot 140 and the horizontal actuators 72 associated with each reactor assembly 50. The microcontroller 180 interfaces with stir motor drivers 184 that are used to drive each of the stir motors 67. The microcontroller 180 also interfaces with heater controllers 186. The heater controllers 186 are used to modulate the heating of the three heater elements 58 within each reactor assembly 50. The microcontroller 180 also receives an input from a radiation amplifier 188 that amplifies respective signals from the radiation sensors 74.

Still referring to FIG. 9, the microcontroller 180 interfaces with a HPLC controller 190. The HPLC controller controls the HPLC injection valve 134 and receives an input signal from the loop loading sensor 192. The microcontroller 180 also interfaces with valve drivers and position sensors 194. Valves are driven to selectively actuate pressure from inert gas that passes through pressure regulations 172. For example, stopcock actuators 100 are actuated to move stopcock valves 102 located within the cassettes 80. Likewise, the valve drivers and position sensors 194 are used to actuate the vertical actuators 70 of the reactor assemblies 50. Valve drivers and position sensors 194 can also be used to push reagents or the like from an external source into the synthesizer 12. Microcontroller 180 also controls the vacuum pump 196 that pulls vacuum through the vacuum port 154 of the reagent and gas handling robot 140. A cold trap 198 is provided to condense any vapors and prevent contamination of the vacuum pump 196.

The automated synthesizer 10 performs radiosynthesis by completing a sequence of chemistry unit operations such as listed in Table 1 below. The interaction among the subsystems and disposable cassettes 80 to carry out each operation are described below.

TABLE 1

UNIT OPERATIONS USABLE TO BUILD A SYNTHESIS SEQUENCE

| Unit Operation | Description of function |
| --- | --- |
| INITIALIZE | Initializes hardware. |
| TRAPF18 | Trap [$^{18}$F]fluoride from cyclotron or preloaded external vial. |
| ELUTEF18 | Elute [$^{18}$F]fluoride with a reagent from the cassette. |
| ADD | Add a reagent from any cassette. |
| EVAPORATE | Evaporate the contents of a reactor. |
| REACT | Fully seal a reaction vessel for a reaction. |
| TRANSFER | Transfer solvents and reaction products from one reaction vessel to another, often using purification cartridges in between. |
| TRANSFERTOHPLC | Transfers the contents of the reaction vessel to the HPLC injection loop. |
| EXTERNALADD | Move a reactor to its add position for externally adding a reagent. |
| MIX | Mix the contents of a reaction vessel. |
| MOVE | Move a reactor to a given position. |

Radioisotope Handling

Typically, in nucleophilic fluorine-18 radiochemistry, [$^{18}$F]fluoride is trapped on a strong anion exchange resin such as quaternary methylammonium (QMA) resin for purification and recovery of [$^{18}$O]H$_2$O and released in a solution with lower water content to reduce the time needed for drying. The preconditioned purification cartridge 132 (e.g., QMA cartridge) is installed with Luer fittings between two tubes coming from the cassette 80, and the source of [$^{18}$F]fluoride (vial or cyclotron) via another tube. If an external vial is used, an external inert gas delivery line is available to pressurize the vial for delivery on demand. Alternatively, the gas delivery system of the cyclotron can be used to directly push the [$^{18}$F]fluoride into the automate synthesizer 10. During trapping, the [$^{18}$F]fluoride source solution flows through the QMA cartridge where [$^{18}$F] fluoride is retained and the carrier [$^{18}$O]H$_2$O, then flows into the recovery vial in the cassette 80. During elution, stopcock valve 102 positions are switched and the gas handling robot 140 drives the eluent from the eluent addition position of the cassette 80 through the QMA cartridge 132 and into the reactor vial 52. Multiple elutions can be performed to increase efficiency of [$^{18}$F]fluoride collection. PEEK tubing can be used for all fluid paths involving [$^{18}$F]fluoride to maximize specific activity. For other radioisotopes, a purification cartridge 132 may not be necessary and can be bypassed. Radioisotopes may be added to any of the three reactors independently.

Reagent Handling

Figure 10A:
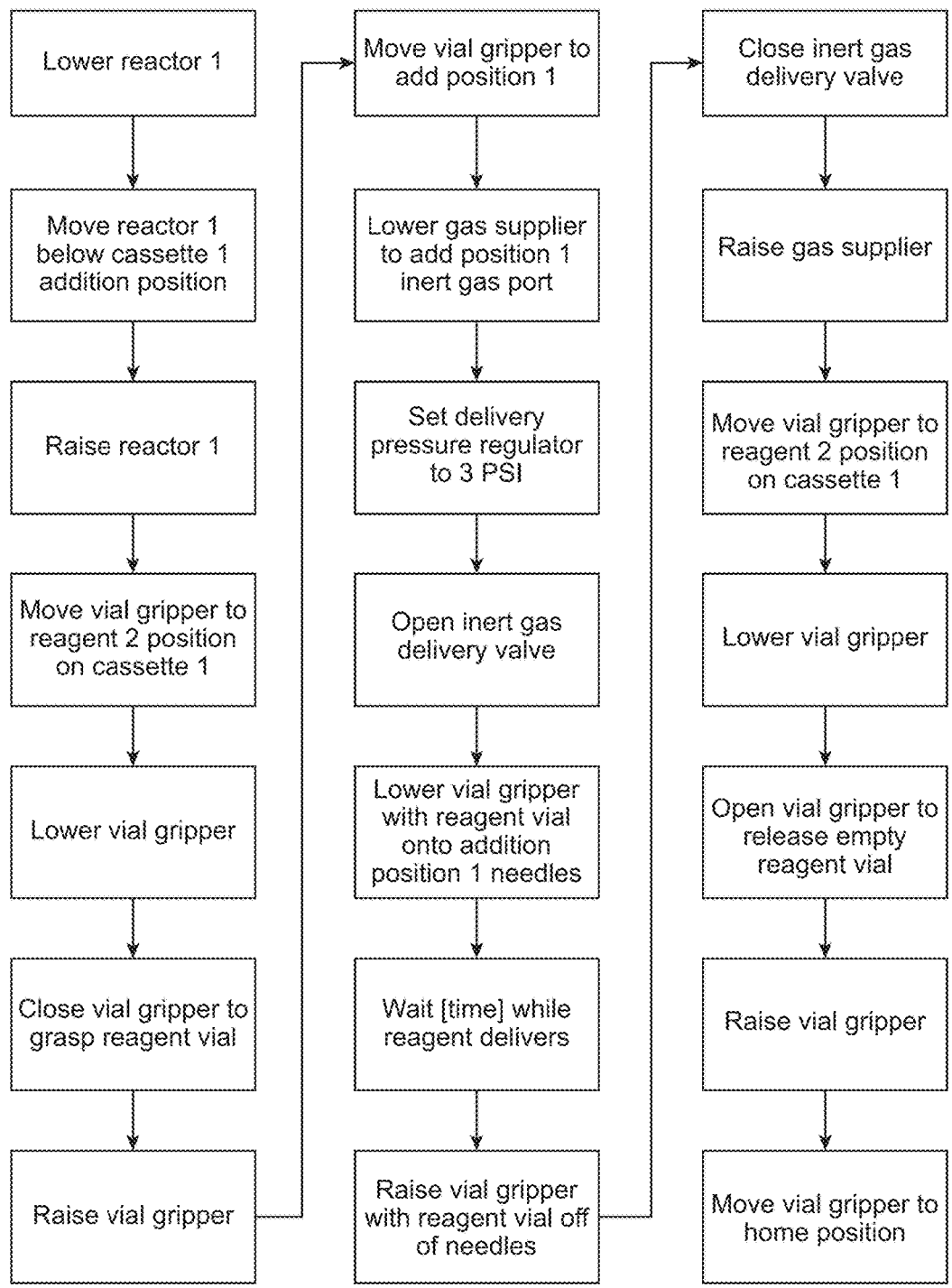
FIG. 10A illustrates a summarized view of each step that makes up the operation of material addition.
Figure 10B:
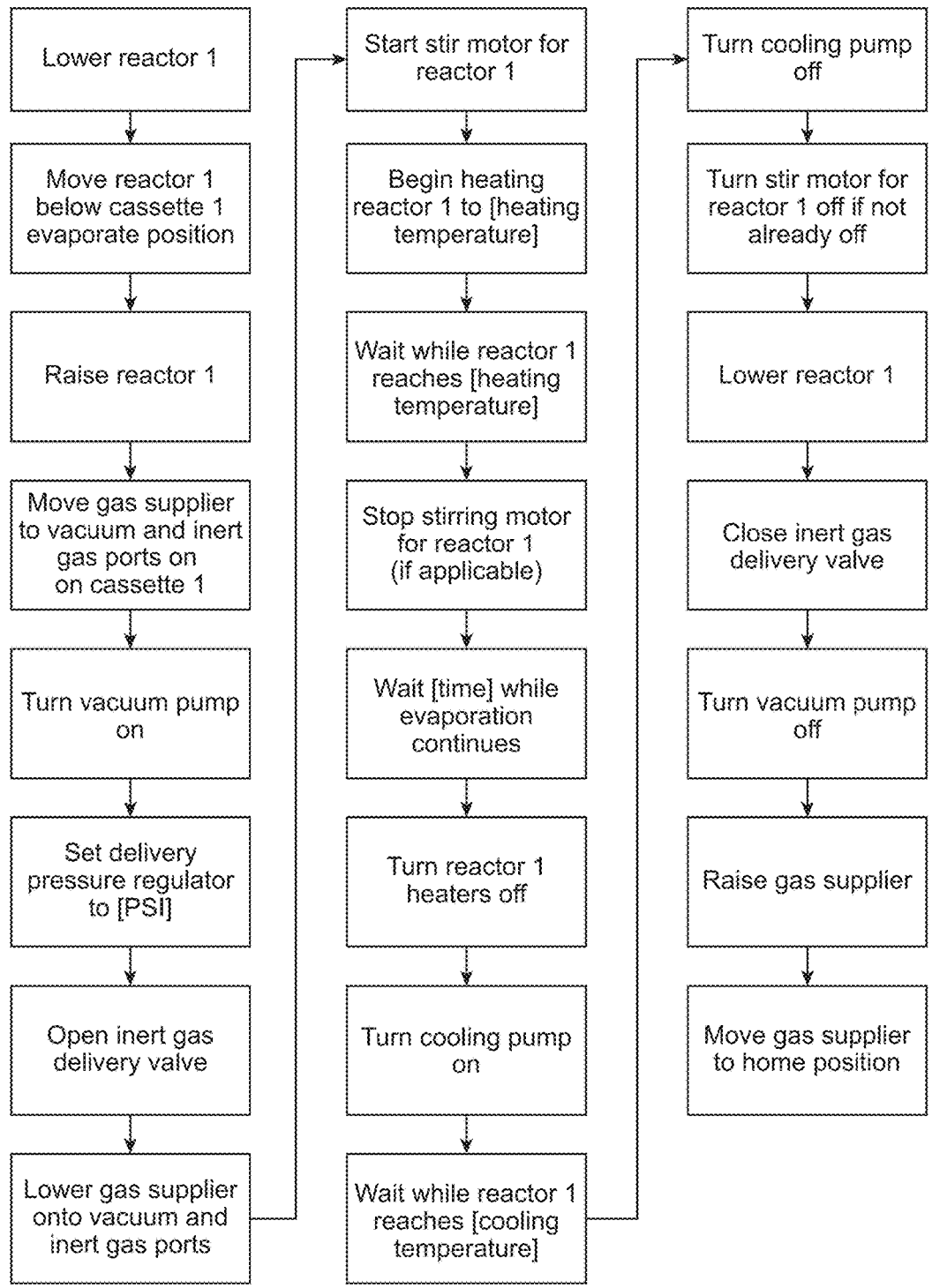
FIG. 10B illustrates a summarized view of a flow diagram showing the sequence of low level steps required to evaporate the contents of the first reactor vial.

To add a particular reagent, the vial gripper 158 moves to the vial storage positions 88, lowers to the storage vial 84, grasps the vial 84, lifts the vial 84, and moves it to the designated reagent addition location 108 on the specified cassette 80. To deliver the reagent to the reactor vial 52 within the reactor assembly 50, the vial gripper 158 lowers the vial 84 down onto a pair of needles 110, 112 in one of the two reagent addition positions 108a, 108b or eluent addition position 108c, and the gas manifold 152 is lowered to pressurize the vial 84, which causes transfer of its contents. The required time for addition of a reagent is generally determined by repeatedly measuring the time needed for complete transfer of the desired liquid and volume at the desired pressure, taking the maximum value, and multiplying by a safety factor. The entire contents of the reagent vial 84 are delivered at once. After addition is complete, the vial gripper 158 lifts the empty reagent vial 84, the gas manifold 152 disengages, and the vial 84 is returned to its original storage position. FIG. 10A shows a summarized view of each step that makes up the operation of material addition. Like all fluidic systems, there are losses associated with dead volumes during liquid transfers. Initial characterization revealed that 120 μL±20 μL (n=120) of the liquid remains in the reagent vial after addition. To account for this loss, additional reagent can be loaded into the crimped vials. FIG. 10B illustrates a summarized view of a flow diagram showing the sequence of low level steps required to evaporate the contents of the first reactor vial 52.

Reactions

To maintain high internal pressure, the reaction vial 52 is sealed by firmly pressing upward against the gasket 90 on the bottom of the cassette. Each cassette 80 has two independent reaction positions at gaskets 90b, 90c to support up to two separate sealed reactions in each reaction vial 42. To characterize the seal integrity, ~1 mL of anhydrous acetonitrile was sealed and heated at 165° C. for one hour. In all experiments, <14 μL of volume was lost (<1.5%). However, it is believe the actual loss of vapor to be less because small droplets of solvent were observed on the gasket surface and were therefore not included in the measured content of the reaction vessel after the integrity test.

Figure 11:
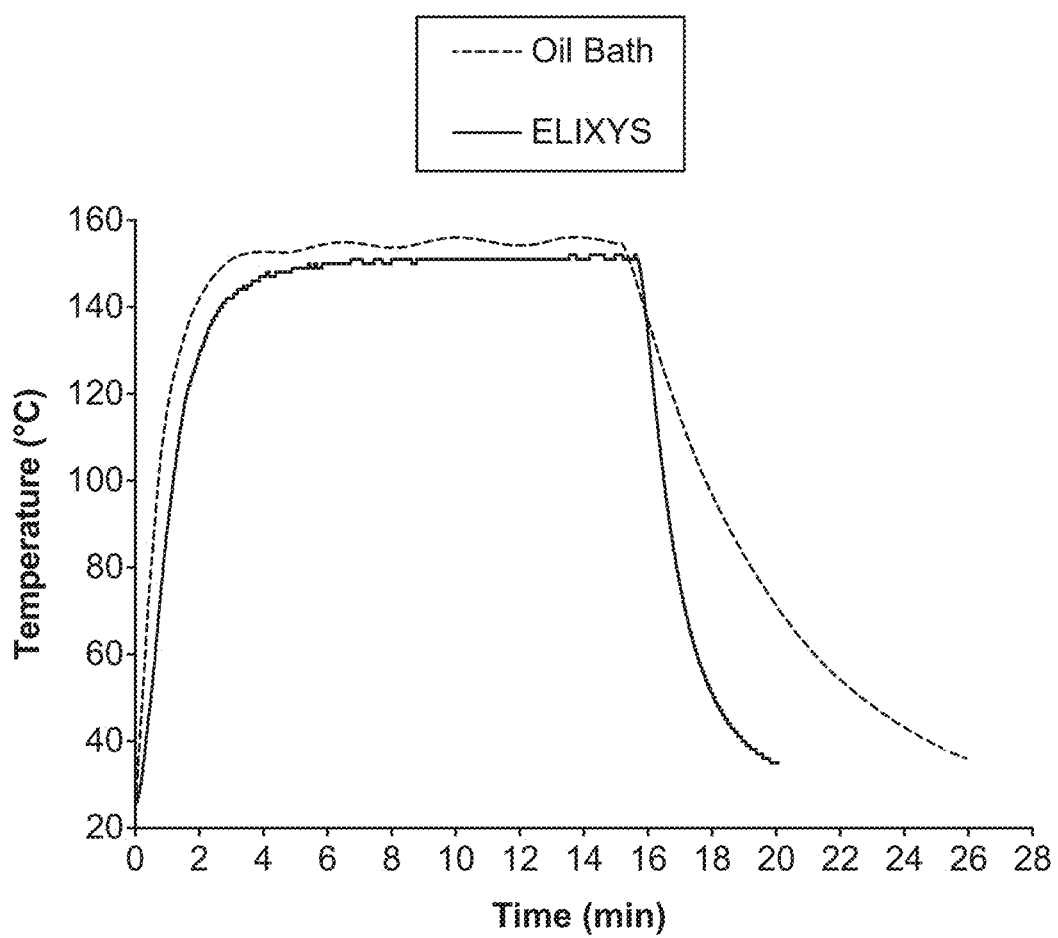
FIG. 11 illustrates is a graph showing the internal temperature of liquid in the reactor vial during heating and cooling in the ELIXYS automated synthesizer system compared to the temperature using an oil bath.

Using a hypodermic needle thermocouple (HN-7-K-TEF, J-KEM Scientific; Saint Louis, Mo., USA) pierced through the gasket, the internal liquid temperature of the reaction vial 52 contents for the automated synthesizer 10 was compared with that and obtained when using the same vessel in a traditional pre-heated oil bath. The comparison of internal liquid temperatures was performed as follows. The reaction vessel was filled with ~1 mL of acetonitrile with a hypodermic thermocouple tip submerged in the liquid. For the automated synthesizer 10 test, the reactor assembly 50 was heated to 160° C., sealed against a modified cassette with protruding thermocouple and held at temperature for 15 min. For the oil bath test, the reaction vessel was sealed with a silicone stopper pierced with the thermocouple and placed in the preheated 160° C. oil bath for 15 min. Active cooling was used for the automated synthesizer 10 and passive ambient air cooling was used for the oil bath, as is conventional for most oil bath heated systems. As FIG. 11 shows, ramping time for heating the solvent is comparable. Both temperatures stabilize at a temperature slightly lower than the set point. This is normal in all radiosynthesizers if the set point is above the solvent boiling point, with the difference depending on the unique thermal characteristics (i.e. heat sources and heat sinks) of the system. Also shown in FIG. 11, the automated synthesizer 10 cools the solvent much faster than simply removing the vessel from the oil bath. If compressed-air cooling is used, the cooling rate is intermediate between these rates (data not shown). It was found that the heating rates and internal liquid temperature are comparable, but the active liquid cooling of the automated synthesizer 10 results in a more rapid decrease in temperature after heating.

After reagents are loaded into the reaction vial 52, a reaction can be performed by sealing the reaction vial 52 against a sealing positions on the gaskets 90b, 90c of the cassette 80. The reactor assembly 50 is then heated to the desired temperature, with optional stirring using motor 67. Once the desired elevated temperature is reached, heating and stirring are continued for the desired reaction time. After this time elapses, the heaters 58 are turned off and the cooling pump is activated until the desired reduced temperature is reached.

Evaporations

Evaporation of solvents occurs by sealing the reaction vial 52 against the gasket 90a of the cassette 80 at the evaporate position. The reaction vial 52 is heated with the option of stirring, and the gas manifold 152 provides both vacuum (to remove vapor) and inert gas (to assist with vapor removal) through the ports (vacuum port 120 and inert gas port 114) on the cassette 80. The required time for evaporation is generally determined by measuring the maximum time needed for complete evaporation of solvent from the desired mixture, and multiplying by a safety factor. After the desired evaporation time, the reactor is cooled.

Transfer and Purification

Sep-Pak™ purification cartridges 132, e.g. silica, C18, etc., are connected to designated Luer® fittings on the cassette 80. A dip tube 106 (e.g., made of ⅛" OD Teflon® tubing) is built into the cassette 80 to act as the fluid path for the transfer of crude products. The transfer unit operation begins with the reactor vial 52 sealing against the transfer position on the cassette 80. The gas manifold 152 being moved by the reagent and gas handling robot 140 provides inert gas to pressurize the reactor vial 52. This moves the fluid through the dip tube 106 and to the Sep-Pak™ purification cartridge 132. After the purification cartridge 132, a dedicated stopcock valve 102 in the cassette 80 switches between a fluid path towards a waste collection vial 116 installed on the cassette 80 and a tube that can be plumbed to the input of the next cassette 80. Often, the first step is to trap the crude product onto the purification cartridge 132 (e.g., Sep-Pak™) and allow the residual solution to collect in the waste container 116. The stopcock position is switched, and elution of the desired product into the next reactor vial 52 is then performed by adding the elution solvent to the first reactor vial 50 and repeating the transfer unit operation to elute the product from the cassette 80.

Radiosynthesis

Materials

No-carrier-added [$^{18}$F]fluoride was produced by the (p,n) reaction of [$^{18}$O]H$_2$O (98% isotopic purity, Medical Isotopes; Pelham, N.H., USA) in a RDS-112 cyclotron (Siemens; Knoxville, Tenn., USA) at 11 MeV using a 1 mL tantalum target with Havar® foil. Anhydrous grade acetonitrile, ethyl acetate, toluene, 1,2-dichloroethane, dichloromethane, methanol, hexane, 4,7,13,16,21,24-Hexaoxa-1,10-diazabicyclo[8.8.8]hexacosane (Kryptofix K222), potassium carbonate, potassium bicarbonate, ammonium phosphate monobasic, ammonium acetate, sodium methoxide in methanol, and 33% hydrobromic acid in acetic acid were purchased from Sigma-Aldrich (Milwaukee, Wis., USA). 1N hydrochloric acid was purchased from Fisher Scientific (Pittsburgh, Pa., USA). QMA (WAT023525) and silica cartridges (WAT020520 and WAT043400) were purchased from Waters (Milford, Mass., USA). The QMA cartridge was preconditioned with 10 mL of 1M potassium bicarbonate followed by 10 mL of 0.1 nm filtered 18MΩ water, and the silica cartridges were preconditioned with 10 mL of anhydrous hexane. Precursors for both D-[$^{18}$F]FAC and L-[$^{18}$F]FMAU (i.e. 2-O-(trifluoromethylsulfonyl)-1,3,5-tri-O-benzoyl-alpha-D-ribofuranose, 2-O-(trifluoromethylsulfonyl)-1,3,5-tri-O-benzoyl-alpha-L-ribofuranose, bis(tri-methylsilyl)cytosine, and 5-methyl-2,4-bis[(trimethylsilyl)oxy]pyrimidine were obtained from ABX (Advanced Biochemical Compounds; Radeberg, Germany) 200-proof ethanol was obtained from the UCLA Chemistry Department (Los Angeles, Calif., USA). All reagents were used as received.

Synthesis Protocol

Figure 12:
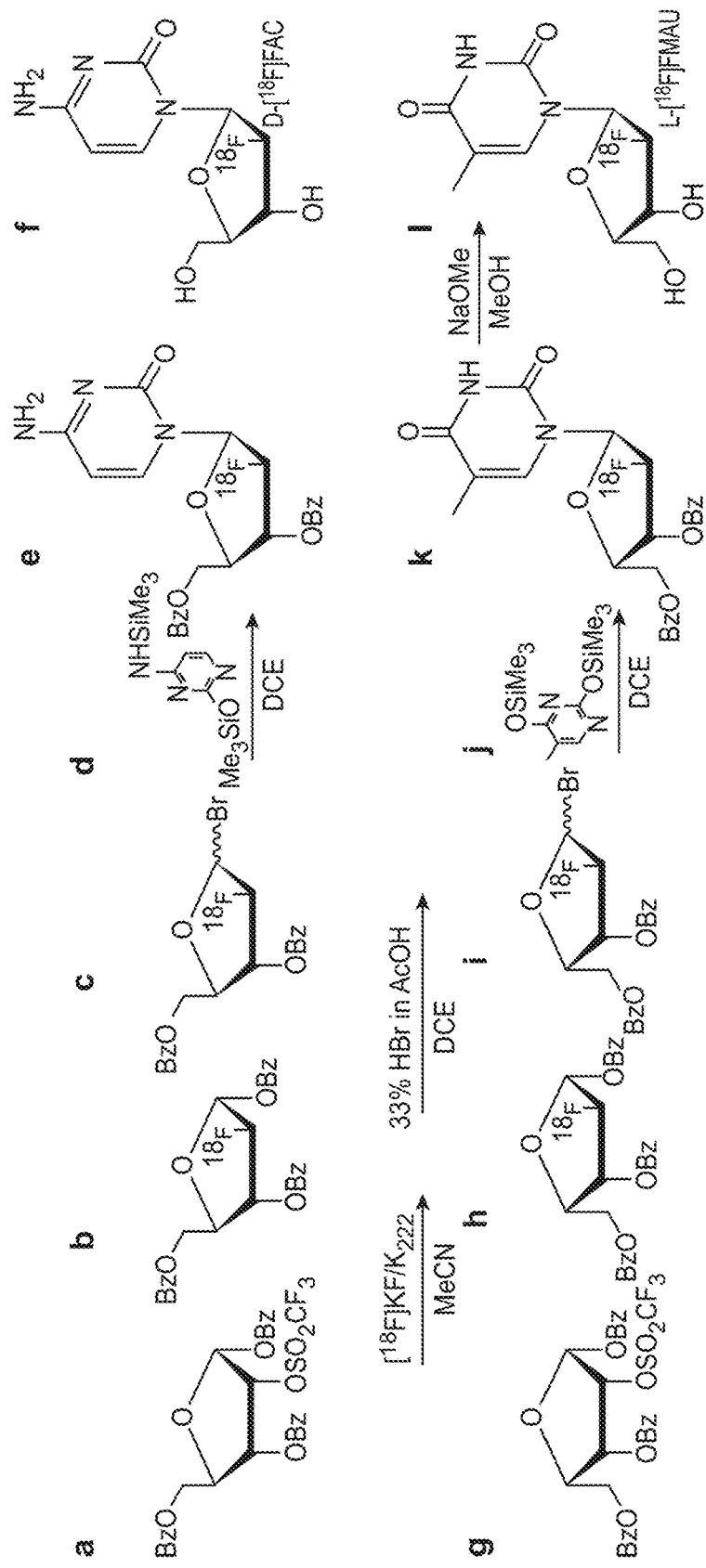
FIG. 12 illustrates the steps in the syntheses of D-[$^{18}$F]FAC (Top) and L-[$^{18}$F]FMAU (Bottom). Synthesis protocol of the two tracers differs only in the ribose sugar (a vs. g) and base coupling (d vs. j) precursors. During HPLC purification, only the beta form is collected as final product.

Synthesis protocols for D-[$^{18}$F]FAC and L-[$^{18}$F]FMAU as seen in FIG. 12 were nearly identical, differing only in precursors and HPLC mobile phases, and were programmed using the drag-and-drop software interface of the automated synthesizer 10 (ELIXYS automated radiochemistry synthesizer by Sofie Biosciences, Culver City, Calif.). A summary of the reagents and unit operations used to synthesize the tracers can be found in Tables 2 and 3 below. Upon completion of each synthesis, the crude product was purified by semi-preparative high-performance liquid chromatography (HPLC) and the desired product (beta form, structures f and l in FIG. 12) was collected and a sample taken for verification and specific activity analysis by analytical HPLC.

TABLE 2

| Reagent ID[a] | Name[b] | Description |
| --- | --- | --- |
| 1-1 | Eluent | 1 mg potassium carbonate and 12 mg of Kryptofix dissolved in 0.800 mL of 3:5 water:acetonitrile |
| 1-2 | MeCN-1 | 1.2 mL, anhydrous |
| 1-3 | MeCN-2 | 1.2 mL, anhydrous |
| 1-4 | Precursor 1 | 10 mg dissolved in 1 mL anhydrous acetonitrile |
| 1-5 | EtOAc-1 | 2 mL, anhydrous |
| 1-6 | EtOAc-2 | 2 mL, anhydrous |
| 2-1 | Toluene | 0.900 mL, anhydrous |
| 2-2 | Precursor 2 | 30 mg ([$^{18}$F]FAC) or 107 mg ([$^{18}$F]FMAU) dissolved in 1 mL anhydrous DCE |
| 2-3 | DCM:MeOH-1 | 2 mL 9:1 (v/v) |
| 2-4 | DCM:MeOH-2 | 2 mL 9:1 (v/v) |
| 2-5 | DCM:MeOH-3 | 2 mL 9:1 (v/v) |
| 3-1 | NaOMe | 0.640 mL of 0.5M in methanol |

TABLE 2-continued

| Reagent ID[a] | Name[b] | Description |
|---|---|---|
| 3-2 | HCl | 0.390 mL of 1N in $H_2O$ |
| 3-3 | HPLC-MP | 1 mL 1:99 EtOH:10 mM $NH_4H_2PO_4$ |
| 2-ExternalAdd1 | HBr | 0.150 mL, 33% in acetic acid |
| 2-ExternalAdd1 | DCE | 0.600 mL, anhydrous DCE |

[a]Notation: Cassette number - reagent position
[b]Name given in the software for referring to the reagents.
Abbreviations:
MeCN, acetonitrile;
Precursor 1, 2-O-(Trifluoromethylsulfonyl)-1,3,5-tri-O-benzoyl-alpha-D-ribofuranose (D-[$^{18}$F]FAC), 2-O-(Trifluoromethylsulfonyl)-1,3,5-tri-O-benzoyl-alpha-L-ribofuranose (L-[$^{18}$F]FMAU);
EtOAc, ethyl acetate;
Precursor 2, bis(trimethylsilyl)cytosine (D-[$^{18}$F]FAC), 5-methyl-2,4-bis[(trimethylsilyl)oxy]pyrimidine (L-[$^{18}$F]FMAU);
DCM, dichloromethane;
MeOH, methanol;
NaOMe, sodium methoxide;
HCl, hydrochloric acid;
HBr, hydrobromic acid;
DCE, 1,2-dichloroethane.

Semi-preparative HPLC was performed with a Well-Chrom K-501 HPLC pump (5 mL/min, Knauer; Berlin, Germany), reversed-phase Gemini-NX column (5 μm, 10×250 mm, Phenomenex; Torrance, Calif., USA), UV detector (254 nm, WellChrom Spectro-Photometer K-2501, Knauer) and gamma-radiation detector and counter (B-FC-3300 and B-FC-1000; Bioscan Inc.; Washington, D.C., USA). The mobile phase for D-[$^{18}$F]FAC was 1% ethanol in 10 mM ammonium phosphate monobasic, and 4% acetonitrile in 50 mM ammonium acetate was used for L-[$^{18}$F]FMAU. Analytical HPLC was done on a Knauer Smartline HPLC system (1 mL/min) with a Phenomenex reverse-phase Luna column (5 μm, 4.6×250 mm) with in-line Knauer UV (254 nm) and gamma-radiation coincidence detector and counter (B-FC-4100 and B-FC-1000). The analytical HPLC mobile phase was 10% ethanol in 50 mM ammonium acetate for D-[$^{18}$F]FAC and 10% acetonitrile in 50 mM ammonium acetate for L-[$^{18}$F]FMAU. All chromatograms were collected by a GINAstar (Raytest USA, Inc.; Wilmington, N.C., USA) analog to digital converter and GINAstar software (Raytest USA, Inc.) running on a PC.

TABLE 3

| # | Unit Operation | Description |
|---|---|---|
| 1 | INITIALIZE | Initializes hardware. |
| 2 | TRAPF18 | Trap [$^{18}$F]fluoride for 120 s at 5 PSI from external vial. |
| 3 | ELUTEF18 | Elute [$^{18}$F]fluoride with Eluent for 120 s at 5 PSI. |
| 4 | EVAPORATE | Evaporate reactor 1 at 110° C. for 300 s with 5 PSI and vacuum. |
| 5 | ELUTEF18 | Elute [$^{18}$F]fluoride with Eluent for 75 s at 5 PSI. |
| 6 | ADD | Add MeCN-1 to reactor 1. |
| 7 | EVAPORATE | Evaporate reactor 1 at 110° C. for 140 s with 5 PSI and vacuum. |
| 8 | ADD | Add MeCN-2 to reactor 1. |
| 9 | EVAPORATE | Evaporate reactor 1 at 110° C. for 140 s with 5 PSI and vacuum. |
| 10 | ADD | Add Precursor 1 to reactor 1. |
| 11 | REACT | React reactor 1 in position 1 for 900 s at 150° C., cooling at 35° C. for 120 s. |
| 12 | TRANSFER | Trap crude product from reactor 1 onto Silica purification cartridge with 10 PSI for 60 s. |
| 13 | ADD | Add EtOAc-1 to reactor 1. |
| 14 | TRANSFER | Elute product from Silica purification cartridge to reactor 2 with 10 PSI for 60 s. |
| 15 | EVAPORATE | Evaporate reactor 2 at 80° C. for 150 s with 5 PSI and vacuum. |
| 16 | ADD | Add EtOAc-2 to reactor 1. |
| 17 | TRANSFER | Elute product from Silica purification cartridge to reactor 2 with 10 PSI for 60 s. |
| 18 | EVAPORATE | Evaporate reactor 2 at 80° C. for 150 s with 5 PSI and vacuum. |
| 19 | EXTERNALADD | Add HBr immediately followed by DCE through ExernalAdd-1 of cassette 2. |
| 20 | REACT | React reactor 2 in position 1 for 600 s at 80° C., cooling to 35° C. for 120 s. |
| 21 | EVAPORATE | Evaporate reactor 2 at 80° C. for 90 s with 5 PSI and vacuum. |
| 22 | ADD | Add Toluene to reactor 2. |
| 23 | EVAPORATE | Evaporate reactor 2 at 110° C. for 140 s with 5 PSI and vacuum. |
| 24 | ADD | Add Precursor 2 to reactor 2. |
| 25 | REACT | React reactor 2 in position 2 for 1800 s at 165° C., cooling to 35° C. for 120 s. |
| 26 | TRANSFER | Trap crude product from reactor 2 onto Silica purification cartridge with 10 PSI for 60 s. |
| 27 | ADD | Add DCM:MeOH-1 to reactor 2. |
| 28 | TRANSFER | Elute product from Silica purification cartridge to reactor 3 with 10 PSI for 45 s. |
| 29 | EVAPORATE | Evaporate reactor 3 at 80° C. for 150 s with 5 PSI and vacuum. |
| 30 | ADD | Add DCM:MeOH-2 to reactor 2. |
| 31 | TRANSFER | Elute product from Silica purification cartridge to reactor 3 with 10 PSI for 45 s. |
| 32 | EVAPORATE | Evaporate reactor 3 at 80° C. for 150 s with 5 PSI and vacuum. |
| 33 | ADD | Add DCM:MeOH-3 to reactor 2. |
| 34 | TRANSFER | Elute product from Silica purification cartridge to reactor 3 with 10 PSI for 45 s. |
| 35 | EVAPORATE | Evaporate reactor 3 at 80° C. for 150 s with 5 PSI and vacuum. |
| 36 | ADD | Add NaOMe to reactor 3. |
| 37 | REACT | React reactor 3 in position 1 for 300 s at 105° C., cooling to 35° C. for 120 s. |
| 38 | ADD | Add HCl to reactor 3. |
| 39 | Mix | Mix the contents of reactor 3 for 20 s. |
| 40 | EVAPORATE | Evaporate reactor 3 at 80° C. for 70 s with 5 PSI and vacuum. |
| 41 | ADD | Add HPLC-MP to reactor 3. |
| 42 | MIX | Mix the contents of reactor 3 for 20 s. |
| 43 | TRANSFERTOHPLC | Transfer contents of reactor 3 to the HPLC injection loop. |

Results and Discussion

To validate the functionality of the automated synthesizer 10, the three-pot syntheses of D-[$^{18}$F]FAC and L-[$^{18}$F]FMAU were performed. Decay corrected radiochemical yield (RCY, d.c.), duration of synthesis, and specific activity are listed Table 4 below.

TABLE 4

|  | Radiochemical yield (%)* | Duration of Synthesis (min)** | Specific Activity (GBq/μmol)*** |
|---|---|---|---|
| [$^{18}$F]FAC | 31 ± 5 (n = 6) | 150 | >37 |
| [$^{18}$F]FMAU | 46 ± 1 (n = 6) | 150 | >111 |

*Decay corrected to start of synthesis
**From start of synthesis to end of synthesis, before HPLC purification.
***Decay corrected to end of synthesis The automated synthesizer 10 produces comparable decay corrected radiochemical yields but with shorter synthesis times (e.g., ~1 hr shorter). Furthermore, the synthesis time of the three-pot synthesis on the automated synthesizer 10 is similar to the one-pot approach reported by others, but the yield on automated synthesizer 10 is substantially higher. Products were confirmed by analytical HPLC, and radiochemical purity was found to be >99% for both tracers. In addition to D-[$^{18}$F]FAC and L-[$^{18}$F]FMAU, the disposable cassette approach allowed for multiple other tracers to be readily synthesized, such as 2-[$^{18}$F]fluoro-2-deoxy-D-glucose ([$^{18}$F]FDG), 3-deoxy-3-[$^{18}$F]fluoro-L-thymidine ([$^{18}$F]FLT), (S)—N-[(1-allyl-2-pyrrolidinyl)methyl]-5-(3-[$^{18}$F]fluoropropyl)-2, 3-dimethoxybenzamide ([$^{18}$F]fallypride), 9-(4-(18)F-Fluoro-3-[hydroxymethyl]butyl)guanine ([$^{18}$F]FHBG), and N-succinimidyl-4-[$^{18}$F]fluorobenzoate ([$^{18}$F]SFB) by switching cassettes 80 and software programs. No hardware or plumbing changes were needed between productions of different tracers. However, one skilled in the art will recognize that the procedures set forth herein are not limited to the specific enumerated reaction and are broadly applicable to preparation of radiosynthesis of a broad range of compounds.

While embodiments of the present invention have been shown and described, various modifications may be made without departing from the scope of the present invention. For example, dimensions illustrated in the drawings are illustrative and may vary from those specifically mentioned therein. The invention, therefore, should not be limited, except to the following claims, and their equivalents.

What is claimed is:

1. An automated radiosynthesizer device comprising:
a plurality of reactor assemblies, each reactor assembly of the plurality being operatively connected to a horizontal actuator for moving the reactor assembly in the horizontal direction and a vertical actuator for moving the reactor assembly in the vertical direction;
a plurality of disposable cassettes disposed above each of the plurality of reactor assemblies, each disposable cassette comprising a lower surface comprising a plurality of sealed and un-sealed gaskets, wherein the un-sealed gaskets are connected to internal fluid paths within the disposable cassette;
a reagent and gas handling robot disposed above the plurality of disposable cassettes and comprising an x-axis actuator, a y-axis actuator, a first z-axis actuator, and a second z-axis actuator, wherein the first z-axis actuator is operatively coupled to a vial gripper and the second z-axis actuator is operatively coupled to a gas manifold; and
a control system configured to control the horizontal actuator and vertical actuator of each reactor assembly and the reagent and gas handling robot.

2. The automated radiosynthesizer device of claim 1, wherein at least one of internal fluid paths terminate at one or more needles projecting from an upper surface of the disposable cassette.

3. The automated radiosynthesizer device of claim 2, wherein the one or more needles comprise a pair of needles with one needle of the pair extending further from the disposable cassette than the other needle.

4. The automated radiosynthesizer device of claim 1, wherein the internal fluid paths include a plurality of valves located within the disposable cassette, the automated radiosynthesizer device comprising valve actuators configured to interface with the plurality of valves.

5. The automated radiosynthesizer device of claim 1, wherein an upper surface of the disposable cassette comprising a plurality of vial storage positions.

6. The automated radiosynthesizer device of claim 1, wherein each cassette further comprises a dip tube extending away from the lower surface of the cassette.

7. The automated radiosynthesizer device of claim 1, wherein each reactor assembly comprises a plurality spring-biased heating assemblies configured to hold a reaction vial.

8. The automated radiosynthesizer device of claim 7, wherein the spring-biased heating assemblies each comprise a coolant fluid path coupled to a cooling system operated by the control system.

9. The automated radiosynthesizer device of claim 1, wherein each reactor assembly comprises a motor coupled to a magnet.

10. The automated radiosynthesizer device of claim 1, wherein each reactor assembly comprises video camera.

11. The automated radiosynthesizer device of claim 1, wherein the vertical actuator comprises a plurality of pneumatic actuators.

12. The radiosynthesizer device of claim 1, further comprising a plurality of gas ports disposed in an upper surface of the disposable cassettes, the plurality of gas ports communicating with the internal fluid paths.

13. The radiosynthesizer device of claim 1, further comprising a conduit connecting one of the plurality of disposable cassettes to another of the plurality of disposable cassettes.

14. The radiosynthesizer device of claim 1, further comprising a purification cartridge operably connected to at least one of the disposable cassettes.

15. The radiosynthesizer device of claim 1, further comprising a HPLC injection valve fluidically coupled to one of the disposable cassettes.

16. The radiosynthesizer device of claim 1, wherein the gas manifold comprises an inert gas port and a vacuum port.

17. An automated method of performing radiosynthesis using a device having a plurality of reactor assemblies, each reactor assembly of the plurality being moveable in a vertical and horizontal direction; a plurality of disposable cassettes disposed above each of the plurality of reactor assemblies, each disposable cassette comprising a lower surface comprising a plurality of sealed and un-sealed gaskets, wherein the un-sealed gaskets are connected to internal fluid paths within the disposable cassette; a reagent and gas handling robot disposed above the plurality of disposable cassettes; and a control system configured to control the movement of the reactor assemblies and the reagent and gas handling robot, the method comprising:

moving a reactor vial contained in a first reactor assembly vertically against one or more of the sealed and unsealed gaskets of a first disposable cassette and performing one or more of the following operations on a radiosynthesis reagent or precursor contained in the reactor vial: addition, evaporation, reaction;

moving a reactor vial contained in a second reactor assembly vertically against one or more of the sealed and unsealed gaskets of a second disposable cassette;

transferring the radiosynthesis reagent or precursor to a second disposable cassette and into the reactor vial contained in the second reactor; and performing one or more of the following operations on a radiosynthesis reagent or precursor contained in the reactor vial contained in the second reactor: addition, evaporation, reaction.

18. The method of claim 17, further comprising moving a reactor vial contained in a third reactor assembly vertically against one or more of the sealed and unsealed gaskets of a third disposable cassette; and transferring the radiosynthesis reagent or precursor to a third disposable cassette and into the reactor vial contained in the third reactor; and performing one or more of the following operations on a radiosynthesis reagent or precursor contained in the reactor vial contained in the third reactor: addition, evaporation, reaction.

19. The method of claim 17, further comprising transferring a final radiosynthesis product to a collection vial or an HPLC injection valve.

20. The method of claim 19, wherein the control system executes a pre-programmed sequence of operations to create the final radiosynthesis product.

* * * * *